(12) United States Patent
Weiner et al.

(10) Patent No.: US 6,838,236 B1
(45) Date of Patent: Jan. 4, 2005

(54) VPR FUNCTION AND ACTIVITY

(75) Inventors: David B. Weiner, Merion, PA (US); David Nathan Levy, Philadelphia, PA (US); Yosef Refaeli, Philadelphia, PA (US)

(73) Assignees: The Trustees of the University of Pennsylvania, Philadelphia, PA (US); The Wistar Institute, Philadelphia, PA (US)

( * ) Notice: Subject to any disclaimer, the term of this patent is extended or adjusted under 35 U.S.C. 154(b) by 1826 days.

(21) Appl. No.: 08/167,608

(22) Filed: Dec. 15, 1993

Related U.S. Application Data

(63) Continuation-in-part of application No. 08/019,601, filed on Feb. 19, 1993, now Pat. No. 5,874,225.

(51) Int. Cl.$^7$ .............................................. C12Q 1/70
(52) U.S. Cl. ...................... 435/5; 435/7.1; 435/7.92; 435/69.1; 435/69.3; 424/188.1; 424/208.1
(58) Field of Search .......................... 424/185.1, 186.1, 424/188.1, 208; 435/7, 7.9, 69.3, 974, 975; 530/350, 826

(56) References Cited

U.S. PATENT DOCUMENTS 4,808,536 A * 2/1989 Chang et al. .................. 435/5

FOREIGN PATENT DOCUMENTS

WO    WO 90/15875    12/1990

OTHER PUBLICATIONS

Harlow and Lane, 1988, Cold Spring Harbor Laboratory, New York, pp. 73 and 124.*
Luckow and Summers, 1988, Biotechnol. 6:47–55.*
Miller, 1989, BioEssays 11:91–95.*
European Patent Office Supplementary European Search Report, dated Nov. 5, 1997, 6 pages.
Hattori, N. et al., "The vpr Gene of HIV–2 is a Transactivator Necessary for viral Expression in Primary Macrophages", *Aids Res. Human Retroviruses*, 1991, 7(2), 177, No. XP 002031072 (Abstract only).
Levy, D.N. et al., "HIV Regulatory Gene Function Analysis in a Rhabdomyosarcoma Cell Line", *Vaccines. Modern Approaches to New Vaccines Including Prevention of Aids*, Tenth Annual Meeting, Cold Spring Harbor, New York, Sep., 1992, 243–249, No. XP 000673175.
Levy, D.N. et al., "Induction of Cell Differentiation by HIV–1 VPR", *Aids Res. Human Retroviruses*, 1994, 10(S1), S92, No. XP 002031073 (Abstract only).
Adachi et al., "Production of Acquired Immunodeficiency Syndrome–Associated Retrovirus in Human and Nonhuman Cells Transfected with an Infectious Molecular Clone,", *J. of Virology*, 59:284–291, 1986.
Aguanno et al., "12–O–Tetradecanoylphorbol–13–Acetate–induced Differentiation of a Human Rhabdomyosarcoma Cell Line," *Cancer Research*, 50:3377–3382.

Arya et al., "Trans–Activator Gene of Human T–Lymphotropic Virus Type III (HTLV–III)," *Science*, 229:69–73, 1985.
Chantal Petit et al., "Human Immunodeficiency Virus Infection Down–Regulates HLA Class II Expression and Induces Differentiation in Promonocytic U937 Cells," *J. Clin. Invest.* 79:1883–1889, 1987.
Cohen et al., "Identification of HIV–1 vpr Product and Function," *J. Acquir. Immune Defic. Syndr.* 3:11–18, 1990.
Cohen et al., "Human Immunodeficiency Virus vpr Product Is a Virion–Associated Regulatory Protein," *J. Virol.* 64:3097–3099, 1990.
Colmenares et al., "The ski Oncogene Induces Muscle Differentiation in Quail Embryo Cells," *Cell*, 59:293–303, 1989.
Dedera et al., "Viral Protein R of Human Immunodeficiency Virus Types 1 and 2 Is Dispensable for Replication and Cytopathogenicity in Lymphoid Cells," *J. of Virol.* 63:3205–3208, 1989.
Fisher et al., "A molecular clone of HTLV–III with biological activity," *Nature*, 316:262–265, 1985.
Gallo et al., "Frequent Detection and Isolation of Cytopathic Retroviruses (HTLV–III) from Patients with AIDS and at Risk for AIDS," *Science* 224:500–503, 1984.
Garrett et al., "Rev Activates Expression of the Human Immunodeficiency Virus Type 1 vif and vpr Gene Products," *J. of Virology*, 65:1653–1657.
Gras–Masse et al., "A synthetic protein corresponding to the entire vpr gene product from the human immunodeficiency virus HIV–1 is recognized by antibodies from HIV–infected patients," *Int. J. Peptide Protein Res.*, 36:219–226, 1990.
Griffin et al., "Activation of HIV gene expression during monocyte differentiation by induction of NF–KB," *Nature* 339:70–73, 1989.
Harada et al., "Tumor Promoter, TPA, Enhances Replication of HTLV–III/LAV," *Virology*, 154:249–258, 1986.
Hattori et al., "The Human immunodeficiency virus type 2 vpr gene is essential for productive infection of human macrophages," *Proc. Natl. Acad. Sci. USA* 87:8080–8084, 1990.

(List continued on next page.)

Primary Examiner—James Housel
Assistant Examiner—J. S. Parkin

(57) ABSTRACT

Pharmaceutical compositions comprising the HIV protein vpr or nucleic acid molecule encoding vpr are disclosed. Also disclosed are methods of treating patients suffering from diseases characterized by hyperproliferating undifferentiated cells such as cancer by administering such compositions. Methods of identifying compounds which have anti-HIV activity are disclosed, in particular, methods of identifying compounds which modulate the activity of vpr and of identifying compounds which inhibit vpr binding to the HIV protein gag.

32 Claims, No Drawings

OTHER PUBLICATIONS

Hiti et al., "Expression of the MyoD1 Muscle Determination Gene Defines Differentiation Capability but Not Tumorigenicity of Human Rhabdomyosarcomas," *Mol. Cell. Biol.,* 9:4722–4730, 1989.

Kozak, M., "Point Mutations Define a Sequence Flanking the AUG Initiator Codon That Modulates Translation by Eukaryotic Ribosomes," *Cell,* 44:283–292, 1986.

Levy et al., "Isolation of Lymphocytopathic Retroviruses from San Francisco Patients with AIDS," *Science* 225:840–842, 1984.

Levy et al., "Induction of Cell Differentiation by Human Immunodeficiency Virus 1 vpr," *Cell* 72:541–550, 1993.

Li et al., "Human Immunodeficiency Virus Type 1 DNA Synthesis, Integration, and Efficient Viral Replication in Growth–Arrested T Cells," *J. Virol.* 67:3969–3977, 1993.

Ling et al., "Optimization of teh Polymerase Chain Reaction with Regard to Fidelity: Modified T7, Taq, and Vent DNA Polymerases," *PCR Meth. Appl.,* 1:63–69, 1991.

Morgenstern et al., "Advanced mammalian gene transfer: high titre retroviral vectors with multiple drug selection markers and a complementary helper–free packaging cell line," *Nucl. Acids Res.,* 18:3587–3596, 1990.

Myers et al., "The Emergence of Simian/Human Immunodeficiency Viruses," *AIDS Res. Hum. Retrovir.,* 8:373–386, 1992.

Ogawa et al., "Mutational Analysis of the Human Immunodeficiency Virus vpr Open Reading Frame," *J. Virol.* 63:4110–4114, 1989.

Ratner et al., "Complete nucleotide sequence of the AIDS virus, HTLV–III," *Nature,* 313:277–284, 1985.

Ratner et al., "Complete Nucleotide Sequences of Functional Clones of the AIDS Virus," *AIDS Res. Hum. Retroviruses,* 3:57–69, 1987.

Reiss et al., "Antibody Response to Viral Proteins U (vpu) and R (vpr) in HIV–1–Infected Individuals," *J. of Acquired Immune Deficiency Syndromes,* 3:115–122, 1990.

Korber et al., "Signature Pattern Analysis: A Method for Assessing Viral Sequence Relatedness," *AIDS Res. Human Retro.,* 8:1549–1560, 1992.

Rich et al., "Increased Susceptibility of Differentiated Mononuclear Phagocytes to Productive Infection with Human Immunodeficiency Virus–1 (HIV–1)," *J. Clin. Invest.* 89:176–183, 1992.

Rose et al., "Frequent Identification of HIV–1 DNa in Bronchoalveolar Lavage Cells Obtained from Individuals with the Acquired Immunodeficiency Syndrome[1–3]," *Am. Rev. Respir. Dis.,* 143:850–854, 1986.

Roulston et al., "Induction of Monocytic Differentiation and NF–kB–like Activities by Human Immunodeficiency Virus 1 Infection of Myelomonoblastic Cells," *J. Exp. Med.* 175:751–763, 1992.

Salahuddin et al., "Human T Lymphotropic Virus Type III Infection of Human Alveolar Macrophages," *Blood,* 68:281–284, 1986.

Schuitemaker et al., "Biological Phenotype of Human Immunodeficiency Virus Type 1 Clones at Different Stages of Infection: Progression of Disease Is Associated with a Shift from Monocytotropic to T–Cell–Tropic Virus Populations," *J. Virol.* 66:1354–1360, 1992.

Shibata et al., "Mutational Analysis of Simian Immunodeficiency Virus From African Green Monkeys and Human Immunodeficiency Virus Type 2," *J. Med. Primatol.,* 19:217–225, 1990.

Shibata et al., "Mutational Analysis of the Human Immunodeficiency Virus Type 2 (HIV–2) Genome in Relation to HIV–1 and Simian Immunodeficiency Virus $SIV_{AGM}$," *J. Virol.* 64:742–747, 1990.

Siegel et al., "Morphological and biochemical differentiation of the human medulloblastoma cell line TE671," *Dev. Brain Res.,* 44:269–280, 1988.

Starcich et al., "Characterization of Long Terminal Repeat Sequences of HTLV–III," *Science,* 227:538–540, 1985.

Stratton et al., "Characterization of the human cell line TE671," *Carcinogenesis,* 10:899–905, 1989.

Valentin et al., "In Vitro Maturation of Mononuclear Phagocytes and Susceptibility to HIV–1 Infection," *J. of Acq. Imm. Def. Synd.,* 4:751–759, 1991.

Weiner et al., "Human Genes Other than CD4 Facilitate HIV–1 Infection of Murine Cells," *Pathobiology,* 59:361–371, 1991.

Weiner et al., "Linkage of tyrosine kinase activity with transforming ability of the p185neu oncoprotein," *Oncogene,* 4:1175–1183, 1989.

Westervelt et al., "Dual Regulation of Silent and Productive Infection in Monocytes by Distinct Human Immunodeficiency Virus Type 1 Determinants," *J. Virol.* 66:3925–3931, 1992.

Wong–Staal et al., "Human Immunodeficiency Virus: The Eighth Gene," *AIDS Res. Hum. Retroviruses* 3:33–39, 1987.

Yu et al., "Open Reading Frame vpr of Simian Immunodeficiency Virus Encodes a Virion–Associated Protein," *J. Virol.* 64:5688–5693, 1990.

Yuan et al., "Human Immunodficiency Virus vpr Gene Encodes a Virion–Associated Protein," *AIDS Res. Hum. Retroviruses,* 6:1265–1271, 1990.

Zack et al., "HIV–1 Production from Infected Peripheral Blood T Cells After HTLV–1 Induced Mitogenic Stimulation," *Science* 240:1026–1029, 1988.

* cited by examiner

VPR FUNCTION AND ACTIVITY

CROSS REFERENCE TO RELATED APPLICATIONS

This application is a continuation in part application of U.S. Ser. No. 08/019,601 filed Feb. 19, 1993, now U.S. Pat. No. 5,874,225, which is incorporated herein by reference.

FIELD OF THE INVENTION

The present invention relates to methods of identifying compounds with anti-HIV activity, to kits for practicing such methods and to reagents useful in such kits and methods. The present invention relates to pharmaceutical compositions, treatment methods and diagnostic methods and kits.

BACKGROUND OF THE INVENTION

Since the demonstration in 1987 that the small open reading frame within HIV-1 designated R encodes a 15 kd protein (Wong-Staal, F., et al., (1987) *AIDS Res. Hum. Retroviruses* 3:33–39), relatively little regarding the function of the viral protein R (vpr) has been reported. The vpr open reading frame is conserved within all genomes of HIV-1 and HIV-2 and within most, if not all, simian immunodeficiency virus (SIV) genomes. VPR is immunogenic in vivo in that a large subset of HIV+ individuals makes antibodies that can react with a bacterially produced vpr peptide (Wong-Staal, F., et al., (1987) *AIDS Res. Hum. Retroviruses* 3:33–39).

The progression from HIV infection to AIDS is in large part determined by the effects of HIV on the cells that it infects, including CD4+ T lymphocytes and macrophages. On the other hand, cell activation, differentiation and proliferation are in turn thought to regulate HIV infection and replication in T cells and macrophages. Gallo, R. C. et al. (1984) *Science* 224:500; Levy, J. A. et al., (1984) *Science* 225:840; Zack, J. A. et al. (1988) *Science* 240:1026; Griffin, G. E. et al., (1988) *Nature* 339:70; Valentin, A. et al. (1991) *J. AIDS* 4:751; Rich, E. A. et al., (1992) *J. Clin. Invest.* 89:176; and Schuitemaker, H. et al. (1992) *J. Virol.* 66:1354. Cell division per se may not be required since HIV and other lentiviruses can proliferate in nonproliferating, terminally differentiated macrophages and growth-arrested T lymphocytes. Rose, R. M. et al. (1986) *Am. Rev. Respir. Dis.* 143:850; Salahuddin, S. Z. et al. (1986) *Blood* 68:281; and Li, G. et al. (1993) *J. Virol.* 67:3969. The ability of lentiviruses, including HIV, to replicate in nonproliferating cells, particularly in macrophages, is believed to be unique among retroviruses and it may be significant that several lentiviruses contain a vpr-like gene. Myers, G. et al. (1992) *AIDS Res. Hum. Retrovir.* 8:373. HIV infection of myeloid cell lines can result in a more differentiated phenotype and increase the expression of factors such as NF-KB which are necessary for HIV replication. Roulston, A. et al. (1992) *J. Exp. Med.* 175:751; and Chantal Petit, A. J. et al. (1987) *J. Clin. Invest.* 79:1883.

The most evidence for the function of the vpr protein comes from several studies reporting the activities of HIV strains that have mutations in the vpr gene. It has been reported that mutations in the vpr gene results in a decrease in the replication and cytopathogenicity of HIV-1, HIV-2, and SIV in primary CD4+T lymphocytes and transformed T cell lines (Ogawa, K., et al., (1989) *J. Virol.* 63:4110–4114; Shibata, R., et al. (1990a). *J. Med. Primatol.* 19:217–225; Shibata, R., et al. (1990b) *J. Virol.* 64:742–747 and Westervelt, P. et al. (1992) *J. Virol.* 66:3925), although others have reported mutated vpr gene had no effect on replication (Dedera, D., et al. (1989) *Virol.* 63:3205–3208). Interestingly HIV-2 mutated for vpr has been reported unable to infect primary monocyte/macrophages (Hattori, N., et al. (1990) *Proc. Natl. Acad. Sci. USA* 87:8080–8084). Transactivation of the HIV long terminal repeat and heterologous promoters by HIV is increased about 3-fold in wild-type versus vpr-negative HIV-1, though the mechanism through which vpr may transactivate transcription is unknown and may be indirect (Cohen, E. A., et al., (1990b) *J. Acquir. Immune Defic. Syndr.* 3:11–18). The relationship between the effects of vpr on promoter activity and viral infectivity is not clear. Vpr protein is incorporated into the viral particle, and this finding has led to the proposition that vpr functions early in infection, following virus penetration and uncoating, and that vpr may interact with cellular regulatory mechanisms important in the establishment of infection (Cohen, E. A., et al. 1990a *J. Virol.* 64:3097–3099; Yu, X. F., et al. (1990) *J. Virol.* 64:5688–5693; and, Yuan, X., et al., (1990) *AIDS Res. Hum. Retroviruses* 6:1265–1271).

The vpr gene of HIV-1 has been shown to induce cellular growth inhibition and differentiation in tumor lines of intermediate differentiation in vitro. Levy, D. N. et al. (1993) *Cell* 72:541. Since vpr protein originates within viral particles, vpr may play a role in establishing productive infection.

SUMMARY OF THE INVENTION

The present invention relates to methods of inducing undifferentiated cells to differentiate. The present invention relates to a method of stimulating undifferentiated cells to differentiate which comprises the step of contacting cells with an amount of vpr protein sufficient to stimulate differentiation. According to some embodiments of the present invention, undifferentiated cells are contacted with vpr protein or a function fragment of vpr protein in order to induce the cells to differentiate. According to some embodiments of the present invention, a nucleic acid molecule that comprises a sequence which encodes vpr protein or a functional fragment of vpr protein is introduced into undifferentiated cells. Expression of the sequence that encodes the vpr protein or the functional fragment of vpr protein results in the production of the vpr protein or the functional fragment of vpr protein within the cell, causing the cell to differentiate. According to some embodiments of the present invention, the sequence which encodes vpr protein or a functional fragment thereof is operably linked to regulatory elements which are necessary for expression of the sequence in the cell. According to some embodiments of the present invention, the nucleic acid molecule is DNA.

The present invention relates to pharmaceutical compositions that comprise vpr protein and a pharmaceutically acceptable carrier. According to some embodiments of the present invention, the pharmaceutical composition comprises a functional fragment of vpr protein and a pharmaceutically acceptable carrier.

The present invention relates to pharmaceutical compositions that comprise a nucleic acid molecule that comprises a sequence which encodes vpr protein and a pharmaceutically acceptable carrier. According to some embodiments of the present invention, the pharmaceutical composition comprises a nucleic acid molecule that comprises a sequence which encodes a functional fragment of vpr protein and a pharmaceutically acceptable carrier. According to some embodiments of the present invention, the pharmaceutical composition comprises a nucleic acid molecule that comprises a sequence which encodes vpr protein or a functional fragment thereof that is operably linked to regulatory elements which are necessary for expression of the sequence in the cell. According to some embodiments of the present invention, a pharmaceutical composition comprises a nucleic acid molecule that is DNA.

The present invention relates to methods of treating individuals diagnosed with or suspected of suffering from diseases characterized by hyperproliferating undifferentiated cells which comprises the step of administering to an individual an amount of vpr protein sufficient to stimulate differentiation of said cells. According to some embodiments, the method of the present invention comprises the steps of administering to such individuals, an effective amount of vpr protein or a functional fragment of vpr protein. According to some embodiments of the present invention, the method of the present invention comprises the steps of administering to such individuals, an effective amount of a nucleic acid molecule that comprises a sequence which encodes vpr protein or a functional fragment of vpr protein. According to some embodiments of the present invention, the sequence that encodes vpr protein or a functional fragment of vpr protein is operably linked to regulatory elements which are necessary for expression of the sequence in cells. According to some embodiments of the present invention, the nucleic acid molecule is DNA. According to some embodiments of the present invention, the disease characterized by hyperproliferating undifferentiated cells is cancer or psoriasis.

The present invention relates to methods of preparing differentiated cells which are useful in pharmaceutical compositions by contacting undifferentiated cells of a known lineage with vpr protein or a functional fragment of vpr protein. The present invention relates to methods of preparing differentiated cells which are useful in pharmaceutical compositions by introducing into undifferentiated cells of a known lineage, a nucleic acid molecule that comprises a sequence which encodes vpr protein or a functional fragment of vpr protein. According to some embodiments of the present invention, the sequence that encodes vpr protein or a functional fragment of vpr protein is operably linked to regulatory elements which are necessary for expression of the sequence in cells. According to some embodiments of the present invention, the nucleic acid molecule is DNA.

The present invention relates to redifferentiated tumor cells. The present invention relates to pharmaceutical compositions that comprise redifferentiated tumor cells induced to redifferentiate by contacting tumor cells with vpr protein or introducing into tumor cells a nucleic acid molecule that comprises a nucleotide sequence that encodes vpr protein. In some embodiments, the redifferentiated tumor cells are derived from hepatocytes, endothelial cells, neurons or pancreatic cells.

The present invention relates to a method of treating an individual suffering from a disease associated with the loss or disfunction of cells which comprises the step of implanting into said individual redifferentiated cells.

The present invention relates to a method of identifying compounds which inhibit vpr from stimulating differentiation of undifferentiated cells which comprises the steps of first contacting, in the presence of a test compound, said cells with an amount of vpr protein sufficient to stimulate differentiation and then observing said cells to determine if cell differentiation occurs.

The present invention relates to a method of identifying compounds that inhibit vpr protein binding to gag protein, also referred to as p55 protein, which comprises the steps of contacting vpr protein and gag protein in the presence of a test compound, determining the level of binding between vpr protein and gag protein and comparing that level to the level of binding that occurs when vpr protein and gag protein are contacted in the absence of a test compound. The present invention relates to a method of identifying compounds which inhibit vpr protein binding to gag which comprises the steps of contacting a fragment of vpr protein that is known to bind to gag protein and gag protein in the presence of a test compound, determining the level of binding between the vpr fragment and the gag protein and comparing that level to the level of binding that occurs when the fragment of vpr protein and gag protein are contacted in the absence of a test compound.

The present invention relates to a kit for identifying compounds which inhibit vpr protein binding to gag which comprises a first container comprising vpr protein and a second container comprising gag protein. Either the vpr protein or the gag protein or both may be detectably labelled. Either the vpr protein or the gag protein may be fixed to a solid phase. The kit may also contain antibodies against vpr protein and/or antibodies against gag protein. The antibodies may be in solution or fixed to a solid phase. The present invention relates to a kit for identifying compounds which inhibit vpr protein binding to gag which comprises a first container comprising a fragment of vpr protein which binds to gag protein and a second container comprising gag protein. Either the fragment of vpr protein or the gag protein or both may be detectably labelled. Either the fragment of vpr protein or the gag protein may be fixed to a solid phase. The kit may also contain antibodies against the fragment of vpr protein and/or antibodies against gag protein. The antibodies may be in solution or fixed to a solid phase.

The present invention relates to a method of identifying compounds which inhibit vpr protein binding to p24 which comprises the steps of contacting vpr protein and p24 protein in the presence of a test compound, determining the level of binding and comparing that level to the level of binding that occurs when vpr protein and p24 protein are contacted in the absence of a test compound. The present invention also relates to methods of identifying compounds which inhibit vpr protein binding to p24 which comprise the steps of contacting vpr protein or a fragment of vpr protein known to bind to p24 protein and p24 protein or a fragment of p24 protein known to bind to vpr protein in the presence of a test compound, determining the level of binding and comparing that level to the level of binding that occurs when the vpr protein or fragment of vpr protein known to bind to p24 protein and p24 protein or a fragment of p24 protein known to bind to vpr protein are contacted in the absence of a test compound.

The present invention relates to a kit for identifying compounds which inhibit vpr protein binding to p24 which comprises a first container comprising vpr protein and a second container comprising p24 protein. Either the vpr protein or the p24 protein or both may be detectably labelled. Either the vpr protein or the p24 protein may be fixed to a solid phase. The kit may also contain antibodies against vpr protein and/or antibodies against p24 protein. The antibodies may be in solution or fixed to a solid phase. The present invention relates to a kit for identifying compounds which inhibit vpr protein binding to p24 which comprises a first container comprising vpr protein or a fragment of vpr protein which binds to p24 protein and a second container comprising p24 protein or a fragment of p24 protein that is known to bind to vpr. One or more proteins included in the kit may be detectably labelled. One or more proteins included in the kit may be fixed to a solid phase. The kit may also contain antibodies against the vpr protein or the fragment of vpr protein and/or antibodies against p24 protein or the fragment of p24. The antibodies may be in solution or fixed to a solid phase.

The present invention relates to a method of identifying compounds which inhibit vpr protein binding to p15 which comprises the steps of contacting vpr protein and p15 protein in the presence of a test compound, determining the level of binding and comparing that level to the level of binding that occurs when vpr protein and p15 protein are contacted in the absence of a test compound. The present invention also relates to methods of identifying compounds which inhibit vpr protein binding to p15 which comprise the steps of contacting vpr protein or a fragment of vpr protein known to bind to p15 protein and p15 protein or a fragment of p15 protein known to bind to vpr protein in the presence of a test compound, determining the level of binding and comparing that level to the level of binding that occurs when the vpr protein or fragment of vpr protein known to bind to p15 protein and p15 protein or a fragment of p15 protein known to bind to vpr protein are contacted in the absence of a test compound.

The present invention relates to a kit for identifying compounds which inhibit vpr protein binding to p15 which comprises a first container comprising vpr protein and a second container comprising p15 protein. Either the vpr protein or the p15 protein or both may be detectably labelled. Either the vpr protein or the p15 protein may be fixed to a solid phase. The kit may also contain antibodies against vpr protein and/or antibodies against p15 protein. The antibodies may be in solution or fixed to a solid phase. The present invention relates to a kit for identifying compounds which inhibit vpr protein binding to p15 which comprises a first container comprising vpr protein or a fragment of vpr protein which binds to p15 protein and a second container comprising p15 protein or a fragment of p15 protein that is known to bind to vpr. One or more proteins included in the kit may be detectably labelled. One or more proteins included in the kit may be fixed to a solid phase. The kit may also contain antibodies against the vpr protein or the fragment of vpr protein and/or antibodies against p15 protein or the fragment of p15. The antibodies may be in solution or fixed to a solid phase.

The present invention relates to a method of identifying compounds which inhibit vpr protein binding to p7 which comprises the steps of contacting vpr protein and p7 protein in the presence of a test compound, determining the level of binding and comparing that level to the level of binding that occurs when vpr protein and p7 protein are contacted in the absence of a test compound. The present invention also relates to methods of identifying compounds which inhibit vpr protein binding to p7 which comprise the steps of contacting vpr protein or a fragment of vpr protein known to bind to p7 protein and p7 protein or a fragment of p7 protein known to bind to vpr protein in the presence of a test compound, determining the level of binding and comparing that level to the level of binding that occurs when the vpr protein or fragment of vpr protein known to bind to p7 protein and p7 protein or a fragment of p7 protein known to bind to vpr protein are contacted in the absence of a test compound.

The present invention relates to a kit for identifying compounds which inhibit vpr protein binding to p7 which comprises a first container comprising vpr protein and a second container comprising p7 protein. Either the vpr protein or the p7 protein or both may be detectably labelled. Either the vpr protein or the p7 protein may be fixed to a solid phase. The kit may also contain antibodies against vpr protein and/or antibodies against p7 protein. The antibodies may be in solution or fixed to a solid phase. The present invention relates to a kit for identifying compounds which inhibit vpr protein binding to p7 which comprises a first container comprising vpr protein or a fragment of vpr protein which binds to p7 protein and a second container comprising p7 protein or a fragment of p7 protein that is known to bind to vpr. One or more proteins included in the kit may be detectably labelled. One or more proteins included in the kit may be fixed to a solid phase. The kit may also contain antibodies against the vpr protein or the fragment of vpr protein and/or antibodies against p7 protein or the fragment of p7. The antibodies may be in solution or fixed to a solid phase.

The present invention relates to a method of identifying compounds which inhibit vpr protein binding to p6 which comprises the steps of contacting vpr protein and p6 protein in the presence of a test compound, determining the level of binding and comparing that level to the level of binding that occurs when vpr protein and p6 protein are contacted in the absence of a test compound. The present invention also relates to methods of identifying compounds which inhibit vpr protein binding to p6 which comprise the steps of contacting vpr protein or a fragment of vpr protein known to bind to p6 protein and p6 protein or a fragment of p6 protein known to bind to vpr protein in the presence of a test compound, determining the level of binding and comparing that level to the level of binding that occurs when the vpr protein or fragment of vpr protein known to bind to p6 protein and p6 protein or a fragment of p6 protein known to bind to vpr protein are contacted in the absence of a test compound.

The present invention relates to a kit for identifying compounds which inhibit vpr protein binding to p6 which comprises a first container comprising vpr protein and a second container comprising p6 protein. Either the vpr protein or the p6 protein or both may be detectably labelled. Either the vpr protein or the p6 protein may be fixed to a solid phase. The kit may also contain antibodies against vpr protein and/or antibodies against p24 protein. The antibodies may be in solution or fixed to a solid phase. The present invention relates to a kit for identifying compounds which inhibit vpr protein binding to p6 which comprises a first container comprising vpr protein or a fragment of vpr protein which binds to p6 protein and a second container comprising p6 protein or a fragment of p6 protein that is known to bind to vpr. One or more proteins included in the kit may be detectably labelled. One or more proteins included in the kit may be fixed to a solid phase. The kit may also contain antibodies against the vpr protein or the fragment of vpr protein and/or antibodies against p6 protein or the fragment of p6. The antibodies may be in solution or fixed to a solid phase.

The present invention relates to a method of identifying compounds which inhibit p24 binding to p15 which comprises the steps of contacting p24 protein and p15 protein in the presence of a test compound, determining the level of binding and comparing that level to the level of binding that occurs when p24 protein and p15 protein are contacted in the absence of a test compound. Fragments of p24 and/or p15 may be used in the method provided that the fragments of p24 are capable of binding to p15 or a fragment thereof and the fragment of p15 is capable of binding to p24 or a fragment thereof.

The present invention relates to a kit for identifying compounds which inhibit p24 protein binding to p15 which comprises a first container comprising p24 protein and a second container comprising p15 protein. Either the p24 protein or the p15 protein or both may be detectably labelled. Either the p24 protein or the p15 protein may be fixed to a solid phase. The kit may also contain antibodies against p24 protein and/or antibodies against p15 protein. The antibodies may be in solution or fixed to a solid phase. The kit may include a container that contains fragments of p24 and/or a container that contains fragments of p15 provided that the fragments of p24 are capable of binding to p15 or a fragment thereof and the fragment of p15 is capable of binding to p24 or a fragment thereof.

The present invention relates to a method of identifying compounds which inhibit p24 binding to p7 which comprises the steps of contacting p24 protein and p7 protein in the presence of a test compound, determining the level of binding and comparing that level to the level of binding that occurs when p24 protein and p7 protein are contacted in the absence of a test compound. Fragments of p24 and/or p7 may be used in the method provided that the fragments of p24 are capable of binding to p7 or a fragment thereof and the fragment of p7 is capable of binding to p24 or a fragment thereof.

The present invention relates to a kit for identifying compounds which inhibit p24 protein binding to p7 which comprises a first container comprising p24 protein and a second container comprising p7 protein. Either the p24 protein or the p7 protein or both may be detectably labelled. Either the p24 protein or the p15 protein may be fixed to a solid phase. The kit may also contain antibodies against p24 protein and/or antibodies against p7 protein. The antibodies may be in solution or fixed to a solid phase. The kit may include a container that contains fragments of p24 and/or a container that contains fragments of p7 provided that the fragments of p24 are capable of binding to p7 or a fragment thereof and the fragment of p7 is capable of binding to p24 or a fragment thereof.

The present invention relates to a method of identifying compounds which inhibit p24 aggregation which comprises the steps of maintaining p24 protein under conditions which promote its aggregation in the presence of a test compound, determining the level of p24 aggregation and comparing that level to the level of aggregation that occurs when p24 protein is maintained under the same conditions in the absence of a test compound. According to some embodiments, conditions which promote p24 aggregation include the presence of p15 or a monoclonal antibody 1238.

The present invention relates to a kit for identifying compounds which inhibit p24 aggregation which comprises a first container comprising p24 protein and a second container comprising p15 protein or MAb 1238.

The present invention relates to methods of identifying individuals exposed to HIV by detecting presence of vpr protein in sample using antibodies which were produced in response to exposure to vpr protein produced in eukaryotic cells. The antibodies are preferably monoclonal antibodies. The antibodies are preferably raised against vpr made in human cells, CHO cells, insect cells or yeast cells. Quantification of the amount of vpr protein present in a sample of an individual may be used in determining the prognosis of an infected individual as the level of vpr in an infected individual may be indicative of the progress of infection.

The present invention relates to antibodies which are produced in response to exposure to vpr protein produced in eukaryotic cells. The antibodies are preferably monoclonal antibodies. The antibodies are preferably raised against vpr made in human cells, CHO cells, insect cells or yeast cells.

The present invention relates to kits for identifying individuals exposed to HIV comprising a first container which contains antibodies which were produced in response to exposure to vpr protein produced in eukaryotic cells and a second container which contains vpr protein produced in eukaryotic cells. The antibodies are preferably monoclonal antibodies. The antibodies are preferably raised against vpr made in human cells, CHO cells, insect cells or yeast cells. The vpr is preferably made in human cells, CHO cells, insect cells or yeast cells. The kits may be adapted for quantifying of the amount of vpr protein present in a sample of an individual. Such information may be used in determining the prognosis of an infected individual as the level of vpr in an infected individual may be indicative of the progress of infection.

The present invention relates to methods of identifying individuals exposed to HIV by detecting presence of antibodies against vpr protein in sample using vpr protein produced in eukaryotic cells. The vpr is preferably produced in human cells, CHO cells, insect cells or yeast cells. Quantification of the amount of anti-vpr antibodies present in a sample of an individual may be used in determining the prognosis of an infected individual as the level of anti-vpr antibodies in an infected individual may be indicative of the progress of infection.

The present invention relates to vpr protein produced in eukaryotic cells. The vpr is preferably produced in human cells, CHO cells, insect cells or yeast cells.

The present invention relates to kits for identifying individuals exposed to HIV comprising a first container which contains antibodies which were produced in response to exposure to vpr protein produced in eukaryotic cells and a second container which contains vpr protein produced in eukaryotic cells. The vpr is preferably produced in human cells, CHO cells, insect cells or yeast cells. The antibodies are preferably raised against vpr made in human cells, CHO cells, insect cells or yeast cells. The kits may be adapted for quantifying the amount of anti-vpr antibodies present in a sample of an individual. Such information may be used in determining the prognosis of an infected individual as the level of anti-vpr antibodies in an infected individual may be indicative of the progress of infection.

The present invention relates to a method of enhancing retroviral propagation in cell culture by contacting the cells with vpr protein in conjunction with infection of the cells by retrovirus. The vpr protein may be added before, after or simultaneously with the retrovirus.

The present invention relates to a method of enhancing retroviral propagation in cell culture by introducing into the cells a nucleic acid molecule that comprises a sequence that encodes vpr protein in conjunction with infection of the cells by retrovirus. The nucleic acid molecule that comprises a sequence that encodes vpr protein may be introduced into the cells before, after or simultaneously with the retrovirus.

The present invention relates to methods of identifying compounds which inhibit vpr's ability to enhance retroviral replication by infecting cells with a retrovirus in the presence of vpr protein and a test compound and comparing the amount of virus produced as a result of such infection to the amount of virus produced in an identical infection protocol except in the absence of test compound.

The present invention relates to methods of increasing the sensitivity of detection of HIV and other retroviruses in a quantitative virus load assay by including a step in the assay which comprises adding vpr. Since vpr enhances viral replication, the viral load assays results will be exaggerated and therefore more sensitive.

The present invention relates to methods of identifying compounds which inhibit vpr's ability to enhance retroviral replication by infecting cells that produce vpr protein with a retrovirus in the presence of vpr protein and a test compound and comparing the amount of virus produced as a result of such infection to the amount of virus produced in an identical infection protocol except in the absence of test compound. The cells comprise a nucleic acid molecule that comprises a sequence that encodes vpr protein.

The present invention relates to methods of modifying macrophage state of differentiation by contacting macrophage cells with vpr protein.

The present invention relates to methods of modifying macrophage state of differentiation by introducing into the macrophage cells a nucleic acid molecule that comprises a sequence that encodes vpr protein.

The present invention relates to methods of treating individuals diagnosed with or suspected of suffering from diseases characterized by undesirable activity of macrophage cells. According to some embodiments, the method of the present invention comprises the steps of administering to such individuals, an effective amount of vpr protein or a functional fragment of vpr protein. According to some embodiments of the present invention, the method of the present invention comprises the steps of administering to such individuals, an effective amount of a nucleic acid molecule that comprises a sequence which encodes vpr protein or a functional fragment of vpr protein. According to some embodiments of the present invention, the sequence that encodes vpr protein or a functional fragment of vpr protein is operably linked to regulatory elements which are necessary for expression of the sequence in cells. According to some embodiments of the present invention, the nucleic acid molecule is DNA. According to some embodiments of the present invention, the disease characterized by undesirable activity of macrophage cells is an autoimmune disease or a granuloma.

The present invention relates to compositions useful for delivering vpr into specifically targeted cells. The composition comprise vpr, p24 and a cell-type specific coat protein assembled as a particle which is a drug delivery particle that can specifically deliver vpr cells that the coat protein binds to. The present invention relates to the particles, to the pharmaceutical compositions that comprise the particles and pharmaceutically acceptable carriers, to the nucleic acid molecules that encode the components, to the expression vectors and host cells that contain the nucleic acid molecules and to the methods of producing and using the compositions.

The present invention relates to compositions useful for delivering fusion compounds into specifically targeted cells. The fusion compound comprises a biologically active portion and a vpr fragment which binds to p24. The compositions comprise the fusion compound, p24 and a cell-type specific coat protein assembled as a particle which is a drug delivery particle that can specifically deliver the fusion compound to cells that the coat protein binds to. The present invention relates to the fusion compounds, to the particles, to the pharmaceutical compositions that comprise the particles and pharmaceutically acceptable carriers, to the nucleic acid molecules that encode the components, to the expression vectors and host cells that contain the nucleic acid molecules and to the methods of producing and using the compositions.

The present invention relates to pharmaceutical compositions that comprise the inactive immunogenic fragments of vpr protein and a pharmaceutically acceptable carrier. The present invention relates to pharmaceutical composition comprising anti-vpr antibodies and a pharmaceutically acceptable carrier.

The present invention relates to a method of treating an individual exposed to HIV by administering an immunogenic amount of inactive immunogenic vpr fragment.

The present invention relates to a method of treating an individual exposed to HIV by administering an immunogenic amount of vpr.

The present invention relates to a method of treating an individual exposed to HIV by administering a therapeutically effective amount of anti-vpr antibodies.

Description of Preferred Embodiments of the Invention

The present invention arises out of the discovery of activities of the HIV regulatory protein vpr (referred to herein as "vpr protein") and its role in HIV replication and infection of cells. It has been discovered that HIV protein vpr induces undifferentiated cells to differentiate, that vpr effects modifies the state of macrophage cells, that vpr binds to HIV protein encoded by the gag gene (also referred to herein as "p55") and the smaller proteins that are generated by processing of p55. It has also been discovered that many of the smaller proteins that are generated by processing of p55 interact with each other and that some of these interactions are directly linked to aggregation of p24 required for viral assembly. Further, it has been discovered that vpr produced in eukaryotic cells can be used to identify individuals infected with HIV as can antibodies that specifically bind to eukaryotic vpr. These activities and functions of vpr allow vpr to be useful in methods of alter cells including cancer cells and cells associated with autoimmune disease and producing cells useful in pharmaceutical compositions as therapeutics, methods of identifying compounds that inhibit HIV infection and/or replication, methods of and kits and reagents for identifying individuals infected with HIV, pharmaceutical compositions, drug delivery systems and methods for specifically targeting vpr and other biologically active agents to specific cells and pharmaceutical compositions useful for and methods of treating individuals infected with HIV. The human protein which vpr protein interacts with has been identified and purified. Some aspects of the invention relate to compositions and methods of treating individuals infected with HIV.

Several aspects of the invention relate to the vpr's ability to induce undifferentiated cells to differentiate. In some embodiments, vpr is used in a pharmaceutical composition to treat individuals suffering from diseases associated with hyperproliferating undifferentiated cells such as cancer or psoriasis. In some embodiments, vpr is used as a reagent to induce undifferentiated cells to differentiate. In some embodiments, undifferentiated tumor cells of specific cell type origin are induced to differentiate back to their prior cell type. Such cells are used in pharmaceutical compositions to treat individuals suffering from diseases characterized by cell destruction or dysfunction of such a cell type. The ability of vpr to stimulate differentiation is believed to assist the virus in replication by producing a desirable environment or conditions, particularly for production of viral particles. Accordingly, in one aspect of the invention, anti-HIV compounds may be identified by identifying compounds that inhibit the activity of vpr to induce differentiation in undifferentiated cells.

The present invention also relates to the use of functional fragments of vpr to induce differentiation of undifferentiated cells and to reagents and pharmaceutical compositions that comprise functional fragments of vpr and to uses of functional fragments of vpr. As used herein, the term "functional fragment of vpr" is meant to refer to a fragment of vpr which retains its ability to induce differentiation of undifferentiated cells. Functional fragment of vpr are at least about 5 amino acids in length derived from vpr and may comprise non-vpr amino acid sequences. One having ordinary skill in the art can readily determine whether a protein or peptide is a functional fragment of vpr by examining its sequence and testing its ability to differentiate undifferentiated cells without undue experimentation. Truncated versions of vpr may be prepared and tested using routine methods and readily available starting material. As used herein, the term "functional fragment" is also meant to refer to peptides, polypeptides, amino acid sequence linked by non-peptidal bonds, or proteins which comprise an amino acid sequence that is identical or substantially homologous to at least a portion of the vpr protein amino acid sequence and which are capable of inducing a hyperproliferating undifferentiated cell to differentiate. The term "substantially homologous" refers to an amino acid sequence that has conservative substitutions. One having ordinary skill in the art can produce functional fragments of vpr protein following the disclosure provided herein and well known techniques. The functional fragments thus identified may be used and formulated in place of full length vpr without undue experimentation.

Therapeutic aspects include use of vpr, a functional fragment of vpr, nucleic acid molecules encoding vpr or nucleic acid molecules encoding a functional fragment of vpr in pharmaceutical compositions useful to treat an individual suffering from diseases associated with hyperproliferating undifferentiated cells such as cancer or psoriasis. Additionally, cells differentiated using vpr, a functional fragment of vpr, nucleic acid molecules encoding vpr or nucleic acid molecules encoding a functional fragment of vpr may be used as therapeutic cell compositions for diseases characterized by loss or malfunctioning of cells, such as Parkinson's disease. "vpr"-differentiated cells may be implanted or otherwise introduced into such individuals to provide them with functioning differentiated cells which can replace lost cells or function in place malfunctioning cells.

One aspect of the present invention is to use vpr, a functional fragment of vpr, nucleic acid molecules encoding vpr or nucleic acid molecules encoding a functional fragment of vpr in a pharmaceutical composition to combat diseases that are characterized by the hyperproliferation of undifferentiated cells such as cancer or psoriasis. According to the invention, pharmaceutical compositions are provided which comprise either vpr protein or a functional fragment thereof or a nucleic acid molecule which comprises a DNA or RNA sequence that encodes vpr protein or a functional fragment thereof.

One aspect of the present invention relates to pharmaceutical compositions that comprise HIV protein vpr or a functional fragment thereof and a pharmaceutically acceptable carrier or diluent. Pharmaceutical compositions comprising vpr protein or a functional fragment thereof are useful for treating an individual having a pathology or condition characterized by hyperproliferating undifferentiated cells. As described herein, pharmaceutical compositions useful for treating diseases characterized by hyperproliferating undifferentiated cells may include vpr protein or a functional fragment thereof since vpr protein or a functional fragment thereof are by definition agents which induce undifferentiated cells to differentiate. Pharmaceutical compositions of the present invention are particularly useful for treating cancer characterized by solid tumors. The ability to stimulate hyperproliferating undifferentiated cells to differentiate provides a means to disrupt the hyperproliferation of the cells. In diseases such as cancer and psoriasis which are characterized by the hyperproliferation of undifferentiated cells, the pharmaceutical composition is useful to stimulate the undifferentiated cells to differentiate. When hyperproliferating undifferentiated cells are induced to differentiate, they cease proliferating and eventually die.

Accordingly, another aspect of the present invention is a method of treating an individual suffering from a disease associated with hyperproliferating undifferentiated cells which comprises the step of administering to said individual an amount of vpr protein sufficient to stimulate differentiation of said cells.

Vpr may be produced by routine means using readily available starting materials as described above. The nucleic acid sequence encoding vpr as well as the amino acid sequence of the protein are well known. The entire HIV genome is published. The long terminal repeat sequences are reported in Stacich, B. et al., (1985) *Science* 227:538–540. Complete nucleotide sequences are reported in Ratner, L. et al., (1985) *Science* 313:277–284 and Ratner, L. et al., (1987) *AIDS Res. Hum. Retroviruses* 3:57–69. The DNA sequence of HIV-1/3B is published in Fisher, A., 1985 *Nature* 316:262. The HIV-1 HXB2 strain nucleotide sequence is available on line from Genbank accession number K03455. The HIV DNA sequence is published in Reiz, M. S., 1992 *AIDS Res. Human Retro.* 8:1549. The sequence is accessible from Genbank No.: M17449. Each of these references including the publicly available sequence information are incorporated herein by reference.

DNA molecules that encode vpr are readily available to the public. Plasmid pNL-43 which contains a DNA sequence encoding HIV-1 strain MN including the vpr protein and plasmid pHXB2 which contains a DNA sequence encoding HIV strain HIV-1/3B are both available from AIDS Research Reference and Reagent Program (ARRRP), Division of AIDS, NIAID, NIH, Bethesda, Md.

Provision of a suitable DNA sequence encoding the desired protein permits the production of the protein using recombinant techniques now known in the art. The coding sequence can be obtained by retrieving the DNA sequence from the publicly available plasmids which comprise DNA encoding vpr protein. The DNA sequence may also be obtained from other sources of HIV DNA or can be prepared chemically using a synthesized nucleotide sequence. When the coding DNA is prepared synthetically, advantage can be taken of known codon preferences of the intended host where the DNA is to be expressed.

One having ordinary skill in the art can, using well known techniques, obtain a DNA molecule encoding the vpr protein and insert that DNA molecule into a commercially available expression vector for use in well known expression systems. For example, the commercially available plasmid pSE420 (Invitrogen, San Diego, Calif.) may be used for production in *E. coli*. The commercially available plasmid pYES2 (Invitrogen, San Diego, Calif.) may be used for production in *S. cerevisiae* strains of yeast. The commercially available MaxBac™ (Invitrogen, San Diego, Calif.) complete baculovirus expression system may be used for production in insect cells. The commercially available plasmid pcDNA I (Invitrogen, San Diego, Calif.) may be used for production in may be used for production in mammalian cells such as Chinese Hamster Ovary cells.

One having ordinary skill in the art can use these commercial expression vectors systems or others to produce vpr protein using routine techniques and readily available starting materials.

One having ordinary skill in the art may use other commercially available expression vectors and systems or produce vectors using well known methods and readily available starting materials. Expression systems containing the requisite control sequences, such as promoters and polyadenylation signals, and preferably enhancers, are readily available and known in the art for a variety of hosts. See e.g., Sambrook et al., *Molecular Cloning a Laboratory Manual*, Second Ed. Cold Spring Harbor Press (1989). Thus, the desired proteins can be prepared in both prokaryotic and eukaryotic systems, resulting in a spectrum of processed forms of the protein.

The most commonly used prokaryotic system remains *E. coli*, although other systems such as *B. subtilis* and Pseudomonas are also useful. Suitable control sequences for prokaryotic systems include both constitutive and inducible promoters including the lac promoter, the trp promoter, hybrid promoters such as tac promoter, the lambda phage Pl promoter. In general, foreign proteins may be produced in these hosts either as fusion or mature proteins. When the desired sequences are produced as mature proteins, the sequence produced may be preceded by a methionine which is not necessarily efficiently removed. Accordingly, the peptides and proteins claimed herein may be preceded by an N-terminal Met when produced in bacteria. Moreover, constructs may be made wherein the coding sequence for the peptide is preceded by an operable signal peptide which results in the secretion of the protein. When produced in prokaryotic hosts in this matter, the signal sequence is removed upon secretion.

A wide variety of eukaryotic hosts are also now available for production of recombinant foreign proteins. As in bacteria, eukaryotic hosts may be transformed with expression systems which produce the desired protein directly, but more commonly signal sequences are provided to effect the secretion of the protein. Eukaryotic systems have the additional advantage that they are able to process introns which may occur in the genomic sequences encoding proteins of higher organisms. Eukaryotic systems also provide a variety of processing mechanisms which result in, for example, glycosylation, carboxy-terminal amidation, oxidation or derivatization of certain amino acid residues, conformational control, and so forth.

Commonly used eukaryotic systems include, but is not limited to, yeast, fungal cells, insect cells, mammalian cells, avian cells, and cells of higher plants. Suitable promoters are available which are compatible and operable for use in each of these host types as well as are termination sequences and enhancers, as e.g. the baculovirus polyhedron promoter. As above, promoters can be either constitutive or inducible. For example, in mammalian systems, the mouse metallothionene promoter can be induced by the addition of heavy metal ions.

The particulars for the construction of expression systems suitable for desired hosts are known to those in the art. For recombinant production of the protein, the DNA encoding it is suitably ligated into the expression vector of choice and then used to transform the compatible host which is then cultured and maintained under conditions wherein expression of the foreign gene takes place. The protein of the present invention thus produced is recovered from the culture, either by lysing the cells or from the culture medium as appropriate and known to those in the art.

One having ordinary skill in the art can, using well known techniques, isolate the vpr protein produced using such expression systems.

In addition to producing these proteins by recombinant techniques, automated amino acid synthesizers may also be employed to produce vpr protein. It should be further noted that if the proteins herein are made synthetically, substitution by amino acids which are not encoded by the gene may also be made. Alternative residues include, for example, the ω amino acids of the formula $H_2N(CH_2)_nCOOH$ wherein n is 2-6. These are neutral, nonpolar amino acids, as are sarcosine (Sar), t-butylalanine (t-BuAla), t-butylglycine (t-BuGly), N-methyl isoleucine (N-MeIle), and norleucine (Nleu). Phenylglycine, for example, can be substituted for Trp, Tyr or Phe, an aromatic neutral amino acid; citrulline (Cit) and methionine sulfoxide (MSO) are polar but neutral, cyclohexyl alanine (Cha) is neutral and nonpolar, cysteic acid (Cya) is acidic, and ornithine (Orn) is basic. The conformation conferring properties of the proline residues may be obtained if one or more of these is substituted by hydroxyproline (Hyp).

The pharmaceutical composition comprising vpr protein and a pharmaceutically acceptable carrier or diluent may be formulated by one having ordinary skill in the art with compositions selected depending upon the chosen mode of administration. Suitable pharmaceutical carriers are described in the most recent edition of *Remington's Pharmaceutical Sciences*, A. Osol, a standard reference text in this field.

For parenteral administration, the vpr protein can be, for example, formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques. For example, a parenteral composition suitable for administration by injection is prepared by dissolving 1.5% by weight of active ingredient in 0.9% sodium chloride solution.

The pharmaceutical compositions according to the present invention may be administered as a single doses or in multiple doses. The pharmaceutical compositions of the present invention may be administered either as individual therapeutic agents or in combination with other therapeutic agents. The treatments of the present invention may be combined with conventional therapies, which may be administered sequentially or simultaneously.

The pharmaceutical compositions comprising vpr protein, or fragments or derivatives may be administered by any means that enables the active agent to reach the agent's site of action in the body of a mammal. Because proteins are subject to being digested when administered orally, parenteral administration, i.e., intravenous, subcutaneous, intramuscular, would ordinarily be used to optimize absorption. In addition, the pharmaceutical compositions of the present invention may be injected at a site at or near hyperproliferative growth. For example, administration may be by direct injection into a solid tumor mass or in the tissue directly adjacent thereto. If the individual to be treated is suffering from psoriasis, the vpr protein may be formulated with a pharmaceutically acceptable topical carrier and the formulation may be administered topically as a creme, lotion or ointment for example.

The dosage administered varies depending upon factors such as: pharmacodynamic characteristics; its mode and route of administration; age, health, and weight of the recipient; nature and extent of symptoms; kind of concurrent treatment; and frequency of treatment. Usually, a daily dosage of vpr protein can be about 1 µg to 100 milligrams per kilogram of body weight. Ordinarily 0.5 to 50, and preferably 1 to 10 milligrams per kilogram per day given in divided doses 1 to 6 times a day or in sustained release form is effective to obtain desired results.

Another aspect of the present invention relates to pharmaceutical compositions that comprise a nucleic acid molecule that encodes vpr and a pharmaceutically acceptable carrier or diluent. According to the present invention, genetic material that encodes vpr protein is delivered to an individual in an expressible form. The genetic material, DNA or RNA, is taken up by the cells of the individual and expressed. The vpr protein that is thereby produced can stimulate hyperproliferating undifferentiated cells to differentiate. Thus, pharmaceutical compositions comprising genetic material that encodes vpr protein are useful in the same manner as pharmaceutical compositions comprising vpr protein: for treating an individual having a pathology or condition characterized by hyperproliferating undifferentiated cells. Pharmaceutical compositions of the present invention are particularly useful for treating cancer characterized by solid tumors.

Thus, a further aspect of the present invention relates to a method of treating an individual suffering from a disease associated with hyperproliferating undifferentiated cells which comprises the step of administering to said individual an amount of nucleic acid that comprises a nucleotide sequence that encodes vpr protein operably linked to regulatory elements necessary for expression.

Nucleotide sequences that encode vpr protein operably linked to regulatory elements necessary for expression in the individual's cell may be delivered as pharmaceutical compositions using gene therapy strategies which include, but are not limited to, either viral vectors such as adenovirus or retrovirus vectors or direct nucleic acid transfer. Methods of delivery nucleic acids encoding proteins of interest using viral vectors are widely reported. A recombinant viral vector such as a retrovirus vector or adenovirus vector is prepared using routine methods and starting materials. The recombinant viral vector comprises a nucleotide sequence that encodes vpr. Such a vector is combined with a pharmaceutically acceptable carrier or diluent. The resulting pharmaceutical preparation may be administered to an individual. Once an individual is infected with the viral vector, vpr protein is produced in the infected cells.

Alternatively, a molecule which comprises a nucleotide sequence that encodes vpr can be administered as a pharmaceutical composition without the use of infectious vectors. The nucleic acid molecule may be DNA or RNA, preferably DNA. The DNA molecule may be linear or circular, it is preferably a plasmid. The nucleic acid molecule is combined with a pharmaceutically acceptable carrier or diluent.

According to the invention, the pharmaceutical composition comprising a nucleic acid sequence that encodes vpr protein may be administered directly into the individual or delivered ex vivo into removed cells of the individual which are reimplanted after administration. By either route, the genetic material is introduced into cells which are present in the body of the individual. Preferred routes of administration include intramuscular, intraperitoneal, intradermal and subcutaneous injection. Alternatively, the pharmaceutical composition may be introduced by various means into cells that are removed from the individual. Such means include, for example, transfection, electroporation and microprojectile bombardment. After the nucleic acid molecule is taken up by the cells, they are reimplanted into the individual.

The pharmaceutical compositions according to this aspect of the present invention comprise about 0.1 to about 1000 micrograms of DNA. In some preferred embodiments, the pharmaceutical compositions contain about 1 to about 500 micrograms of DNA. In some preferred embodiments, the pharmaceutical compositions contain about 25 to about 250 micrograms of DNA. Most preferably, the pharmaceutical compositions contain about 100 micrograms DNA.

The pharmaceutical compositions according to this aspect of the present invention are formulated according to the mode of administration to be used. One having ordinary skill in the art can readily formulate a nucleic acid molecule that encodes vpr. In cases where intramuscular injection is the chosen mode of administration, an isotonic formulation is used. Generally, additives for isotonicity can include sodium chloride, dextrose, mannitol, sorbitol and lactose. Isotonic solutions such as phosphate buffered saline may be used. Stabilizers include gelatin and albumin.

Another aspect of the present invention relates to a method of stimulating undifferentiated cells to differentiate which comprises the step of contacting said cells with an amount of vpr protein or a nucleic acid molecule that encodes vpr sufficient to stimulate differentiation.

The present invention relates to cells differentiated by administration of vpr protein or a functional fragment thereof or by incorporation of a nucleic acid molecule that encodes vpr or a functional fragment thereof.

The present invention relates to a method of treating an individual suffering from a disease associated with the loss or disfunction of cells which comprises the step of implanting into said individual redifferentiated cells.

There are a great number of diseases and disorders whose pathology is associated with lost or damaged cells. Such cells may be replaced by converting undifferentiated cells such as tumor cells or stem cells to differentiated cells which can be implanted into an individual by surgical methods.

The cells are chosen based upon their lineage; i.e. if the disease is characterized by a loss or malfunction of brain cells such as Parkinson's disease, cells of neuronal lineage such as neuronal tumor cells or neuronal stem cells are used. The undifferentiated cells are contacted in vitro with vpr protein or they are transfected with a nucleic acid molecule that comprises a nucleotide sequence that encodes vpr protein operably linked to necessary regulatory sequences which allow for expression of the nucleotide sequence in the cells. Upon differentiation, the cells are implanted into the individual by standard surgical procedures. The new differentiated cells assume the role of the lost or malfunctioning cells.

In cases where tumor cells are induced to differentiate, a safety mechanism is preferably used to insure that if the cells again become tumor cells, they can be killed. The cells may be transfected with a selective marker so that if they retransform and become tumor cells, they may be selectively killed by targeted chemotherapy. For example, a tumor cell line may be transfected with both a gene encoding vpr and a second gene encoding Herpes simplex virus thymidine kinase (tk). If, after differentiating and implantation the cells become tumor cells, administration of gancyclovir will kill the implanted cells.

A preferred embodiment of this aspect of the present invention relates to a method of treating individuals suffering from Parkinson's disease and to pharmaceutical compositions which comprises differentiated neuronal cells. According to this embodiment, publicly available cultured tumor cells that are neuronal in lineage may be induced to differentiate by transfection with, on either the same nucleic acid molecule or separate molecules, a DNA sequence that encodes vpr and a DNA sequence that encodes Herpes simplex virus tk. Once differentiated, the cells are implanted into an individual suffering from Parkinson's disease.

Another aspect of the present invention relates to a method of identifying compounds which inhibit vpr from stimulating differentiation of undifferentiated cells which comprises the steps of first contacting, in the presence of a test compound, said cells with an amount of vpr protein sufficient to stimulate differentiation and then observing said cells to determine if cell differentiation occurs. It is believed that vpr's ability to stimulate undifferentiated cells to differentiate is important for the efficient production of viral particles during HIV infection. Identifying compounds which interfere with vpr's stimulation of cell differentiation provides a drug target for combatting the virus.

According to this aspect of the invention, compounds are identified which modulate vpr stimulation of differentiation of undifferentiated cells. An assay is provided which compares differentiation stimulation by vpr in the presence or absence of test compounds. Using this assay, compounds can be identified which modulate vpr stimulatory activity. In particular, compounds can be identified which inhibit vpr stimulatory action. Such compounds may be useful as anti-HIV therapeutics.

The method of the present invention comprises the step of contacting undifferentiated cells with vpr in the presence of a test compound. The cells can then be observed to determine if the vpr induces differentiation. A control may be provided in which vpr is contacted with cells in the absence of test compound. A further control may be provided in which test compound is contacted with cells in the absence of vpr. If the cells contacted with vpr in the presence of test compound do not differentiate, then anti-vpr activity is indicated for the test compound. This can be confirmed if cells contacted with vpr in the absence of test compound differentiate and the cells contacted with test compound in the absence of vpr do not differentiate.

The assay may be performed using many different types of undifferentiated cells and delivery of vpr through a variety of means. Additionally, functional fragments of vpr may be used in place of vpr. One having ordinary skill in the art, following the teachings of the Specification, can readily appreciate the several ways to practice this aspect of the present invention.

Undifferentiated cells include stem cells and transformed cells such as cultured tumor cells. It is preferred that the cell type chosen is one in which the differentiated form is readily distinguishable from undifferentiated cells. In some embodiments of the invention, the preferred cell types are those of the solid muscle tumor alveolar rhabdomyosarcoma such as the cell lines RD, TE671 and D17. MG63 and HOS-TE86, which are examples of osteosarcoma cell lines, may also be used. KG-1, THP-1, U937, HL60, and PLB973 cell lines are examples of myeloid lineage cells which may be used in the assay. Other cell lines that may be used in the assay include human glioblastoma cell line U-138MG, the human glioblastoma/astrocytoma cell line U373MG and the human glioblastoma/astrocytoma cell line U87-MG.

Test compound is provided, preferably in solution. Serial dilutions of test compounds may be used in a series of assays. Test compound may be added at concentrations from 0.01 $\mu$M to 1 M. A preferred range of final concentrations of a test compound is from 10 $\mu$M to 100 $\mu$M. One test compound that is effective to inhibit vpr's activity is an antibody that specifically binds to vpr and prevents it from inducing differentiation of undifferentiated cells.

Vpr may be delivered by a variety of means. In some embodiments of the invention, it is combined with cells as a protein. The vpr protein may be added directly to cell culture medium. Vpr protein may be produced from widely available starting materials using well known techniques, such as described above. A preferred concentration range of the vpr used is about 1 $\mu$g/ml to 1 mg/ml.

Alternatively, vpr may be contacted with undifferentiated cells by introducing into the cell a nucleic acid molecule which comprises a nucleic acid sequence encoding vpr. In such embodiments, the nucleic acid sequence may be introduced as part of an HIV particle, part of a recombinant infectious expression system particle or part of an expression vector such as a plasmid. Additionally linear DNA or RNA may also be introduced into the cell in an expressible form. One having ordinary skill in the art can construct any number of expression vectors or other nucleic molecules designed to produce vpr in cultured cells. Such an expression system may include a vector system to introduce the genetic material or the nucleic acid molecule may be introduced by other standard techniques such as transfection, electroporation or microprojectile bombardment.

Those having ordinary skill in the art can distinguish undifferentiated cells from differentiated cells routinely. Methods of distinguishing differentiated cells from undifferentiated cells include observing morphological, metabolic and biochemical differences between cell stages. For example, differences in size, shape and over all appearance are often profound when comparing an undifferentiated cell from a corresponding differentiated cell. Likewise, differentiation of cells results in changes in the proteins being produced by the cell.

For example, differentiated alveolar rhabdomyosarcoma cells produce high levels of myosin, a muscle protein, relative to the level of myosin produced by undifferentiated alveolar rhabdomyosarcoma cells. When undifferentiated alveolar cells are induced to differentiate, the increase in the presence of myosin may be detected using routine techniques. The means to detect the presence of a protein product are routine and include enzyme assays and ELISA assays. One having ordinary skill in the art can detect the presence or absence of a protein using well known methods.

Specifically, the initial set of cell lines which were studied included RD, TE671 and D17 as representatives of rhabdomyosarcoma (muscle) cell lines. Differentiation markers for these cells include skeletal alpha-actin, myosin, muscle specific creatine kinase, and troponin 1.

The effects of vpr on expression of the differentiated osteoblast phenotype in the osteosarcoma cell lines MG63 and HOS-TE86 can be observed using non-specific markers of alteration in cell function such as morphology and cell proliferation as well as the expression of osteoblastic markers. The osteoblast markers include the expression of mRNA's for osteocalcin, alkaline phosphatase and type I (aI) collagen (by Northern analysis) and the synthesis of osteocalcin (by radioimmunoassay) and alkaline phosphatase (colorimetric assay). The specificity of effects of test compounds on vpr are also compared to compounds effects on other established osteoblast differentiating agents such as retinoid acid and 1,25 dihydroxyvitamin $D_3$.

Differentiation analysis in cell lines KG-1, THP-1, U937, HL60, and PLB973 cell lines, which are of myeloid lineage, include increases in plastic adherence, increased phagocytosis of latex beads, positive staining for alpha-naphthyl acetate esterase and loss of expression of elastase and cathepsin G, for example. Additionally differentiation of myeloid cell lines can be correlated with changes in specific oncogene expression such as decreases in c-myc transcription.

During differentiation of glioblastoma cell lines, such as the human glioblastoma cell line U-138MG, the human glioblastoma/astrocytoma cell line U373MG and the human glioblastoma/astrocytoma cell line U87-MG, there is a decrease in cell proliferation, increases in ornithine decarboxylase, increases in GFAP, transient increases in fos, increases in specific collagen, increases in the cytoplasmic to nuclear rations, pseudopod extension, neurite outgrowth, bipolarity and activated cytoskeletal activity. Additionally, during differentiation of astrocytes increases in fibronectin expression have been reported.

Another aspect of the invention relates to methods of identifying compounds which inhibit vpr protein binding to the full length precursor protein encoded by the gag gene (p55) and to specific smaller proteins generated when p55 is processed by HIV protease. In particular, it has been discovered that vpr binds to p55 precursor gag protein and the protein products of p55 processing by the HIV protease: p24, p15, p7, and p6. As used herein, the term "gag-derived proteins" is meant to refer to the full length precursor protein encoded by the gag gene (p55) and the protein products of p55 processing by the HIV protease: p24, p15, p7 and p6. Thus gag-derived proteins are p55, p24, p15, p7 and p6. Each of these proteins bind to vpr. Accordingly, each may be used in an assay to identify compounds that inhibit binding of vpr to a particular gag-derived protein. The methods comprise the steps of first contacting, in the presence of a test compound, vpr protein and a gag-derived protein and then determining the level of binding. Compounds which interfere with the binding of vpr to a gag-derived protein are useful to impede production of HIV particle which contain vpr. Accordingly, such compounds are useful to inhibit production of fully virulent HIV particles; therefore such compounds will be useful as anti-HIV therapeutics alone or as part of a multi-faceted anti-HIV drug regimen which includes other therapeutics.

To practice these aspects of the invention, vpr protein and gag-derived protein are contacted in the presence of a test compound. The level of binding of the proteins is determined. The resultant level of binding is compared to the known level of binding that occurs when both proteins are contacted with each other. In the absence of a compound that interferes with the binding, the two proteins will bind. As a control, vpr protein and gag-derived protein are contacted in the absence of a test compound.

Test compound is provided, preferably in solution. Serial dilutions of test compounds may be used in a series of assays. Test compound may be added at concentrations from 0.01 µM to 1 M. A preferred range of final concentrations of a test compound is from 10 µM to 100 µM.

Production of vpr protein is described above. A preferred concentration range of the vpr used is about 1 µg/ml to 1 mg/ml. A preferred concentration of the vpr is about 50 µg/ml.

The full length precursor protein encoded by the gag gene, p55, may be produced by routine means using readily available starting materials following the teachings described above for production of vpr. One having ordinary skill in the art can, using well known techniques, obtain a DNA molecule encoding the gag protein and insert that DNA molecule into a commercially available expression vector for use in well known expression systems. One having ordinary skill in the art can, using well known techniques, isolate the p55 protein produced in such expression systems. Similarly, p24, p15, p7 and p6 can be produced and isolated. For example, p55 can be produced as described herein and processed by one having ordinary skill in the art using HIV protease to produce and isolate one or more of p24, p15, p7 and p6 without undue experimentation. Alternatively, one having ordinary skill in the art can, using well known techniques, obtain a DNA molecule encoding the p55 protein and insert a portion of the DNA molecule that encodes p24, p15, p7 or p6 into a commercially available expression vector for use in well known expression systems. One having ordinary skill in the art can, using well known techniques, isolate the protein produced in such expression systems.

A preferred concentration range of gag-derived protein used is about 1 µg/ml to about 1 mg/ml.

The means to detect the presence of a protein product are routine and include enzyme assays and ELISA assays. One having ordinary skill in the art can detect the presence or absence of a protein using well known methods. One having ordinary skill in the art can readily appreciate the multitude of ways to practice a binding assay to detect compounds which modulate the binding of vpr to gag-derived protein. For example, antibodies are useful for immunoassays which detect or quantitate vpr protein binding to gag-derived protein. The immunoassay typically comprises incubating vpr protein and gag-derived protein to allow protein-protein binding in the presence of a detectably labeled high affinity antibody capable of selectively binding to either vpr protein or gag-derived protein, and detecting the labeled antibody which is bound to the protein. Various immunoassay procedures are described in Immunoassays for the 80's, A. Voller et al., Eds., University Park, 1981.

In this aspect of the invention, the antibody or either vpr protein or gag-derived protein may be added to nitrocellulose, or other solid support which is capable of immobilizing proteins. The support may then be washed with suitable buffers followed by treatment with the detectably labeled vpr-specific antibody or the antibody that binds to the gag-derived protein. The solid phase support may then be washed with the buffer a second time to remove unbound antibody. The amount of bound label on said solid support may then be detected by conventional means.

By "solid phase support" or "carrier" is intended any support capable of binding antigen or antibodies. Well-known supports or carriers, include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention. The support configuration may be spherical, as in a bead, or cylindrical, as in the inside surface of a test tube, or the external surface of a rod. Alternatively, the surface may be flat such as a sheet, test strip, etc. Those skilled in the art will know many other suitable carriers for binding antibody or antigen, or will be able to ascertain the same by use of routine experimentation.

The binding activity of a given lot of antibodies may be determined according to well known methods. Those skilled in the art will be able to determine operative and optimal assay conditions for each determination by employing routine experimentation.

Positive control assays may be performed in which no test compound is added.

One of the ways in which the antibodies can be detectably labeled is by linking the same to an enzyme and use in an enzyme immunoassay (EIA), or enzyme-linked immunosorbent assay (ELISA). This enzyme, when subsequently exposed to its substrate, will react with the substrate generating a chemical moiety which can be detected, for example, by spectrophotometric, fluorometric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase.

By radioactively labeling the antibody, it is possible to detect it through the use of a radioimmunoassay (RIA) (see, for example, Work, T. S., et al., *Laboratory Techniques and Biochemistry in Molecular Biology*, North Holland Publishing Company, N.Y., 1978. The radioactive isotope can be detected by such means as the use of a gamma counter or a scintillation counter or by autoradiography. Isotopes which are particularly useful for the purpose of the present invention are: $^{3}H$, $^{125}I$, $^{131}I$, $^{35}S$, $^{14}C$, and, preferably, $^{125}I$.

It is also possible to label the antibody with a fluorescent compound. When the fluorescent labeled antibody is exposed to light of the proper wave length, its presence can then be detected due to fluorescence. Among the most commonly used fluorescent labelling compounds are fluorescein isothiocyanate, rhodamine, phycoerythrin, phycocyanin, allophycocyanin, o-phthaldehyde and fluorescamine.

The antibody can also be detectably labeled using fluorescence-emitting metals such as $^{152}Eu$, or others of the lanthanide series. These metals can be attached to the TNF-specific antibody using such metal chelating groups as diethylenetriaminepentaacetic acid (DTPA) or ethylenediamine-tetraacetic acid (EDTA).

The antibody also can be detectably labeled by coupling to a chemiluminescent compound. The presence of the chemiluminescently labeled antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin. Detection of the vpr-specific antibody or the antibody that binds to the gag-derived protein may be accomplished by a scintillation counter, for example, if the detectable label is a radioactive gamma emitter, or by a fluorometer, for example, if the label is a fluorescent material.

In the case of an enzyme label, the detection can be accomplished by colorometric methods which employ a substrate for the enzyme. Detection may also be accomplished by visual comparison of the extent of enzymatic reaction of a substrate in comparison with similarly prepared standards.

As can be readily appreciated, one of the viral proteins may also be detectable and serve as a reporter molecule instead of or in addition to the antibody.

The components of the assay may be adapted for utilization in an immunometric assay, also known as a "two-site" or "sandwich" assay. In a typical immunometric assay, a quantity of unlabeled antibody (or fragment of antibody) is bound to a solid support that is insoluble in the fluid being tested and a quantity of detectably labeled soluble antibody is added to permit detection and/or quantitation of the ternary complex formed between solid-phase antibody, antigen, and labeled antibody.

Typical and preferred immunometric assays include "forward" assays in which the antibody bound to the solid phase is first contacted with the one of the viral proteins to immobilize it. The second viral protein is added in the presence of the test compound. After a suitable incubation period, the solid support is washed to remove unbound protein. A second antibody is then added which is specific for the second viral protein. The second antibody is preferably detectable. After a second incubation period to permit the labeled antibody to complex with the second viral protein bound to the solid support through the unlabeled antibody and first viral protein, the solid support is washed a second time to remove the unreacted labeled antibody. This type of forward sandwich assay may be a simple "yes/no" assay to determine whether binding has occurred or may be made quantitative by comparing the measure of labeled antibody with that obtained in a control. Such "two-site" or "sandwich" assays are described by Wide, *Radioimmune Assay Method*, Kirkham, Ed., E. & S. Livingstone, Edinburgh, 1970, pp. 199–206).

Other type of "sandwich" assays are the so-called "simultaneous" and "reverse" assays. A simultaneous assay involves a single incubation step wherein the antibody bound to the solid support and labeled antibody, both viral protein and the test compound are added at the same time. After the incubation is completed, the solid support is washed to remove uncomplexed proteins. The presence of labeled antibody associated with the solid support is then determined as it would be in a conventional "forward" sandwich assay.

In the "reverse" assay, stepwise addition first of a solution of labeled antibody to the viral proteins followed by the addition of unlabeled antibody bound to a solid support after a suitable incubation period, is utilized. After a second incubation, the solid phase is washed in conventional fashion to free it of the residue of the sample being tested and the solution of unreacted labeled antibody. The determination of labeled antibody associated with a solid support is then determined as in the "simultaneous" and "forward" assays. In one embodiment, a combination of antibodies of the present invention specific for separate epitopes may be used to construct a sensitive three-site immunoradiometric assay.

In some preferred embodiments, an anti-vpr antibody is fixed to a solid phase. vpr protein is contacted with the fixed antibody to form a complex. The complex is contacted with a gag-derived protein in the presence of a test compound. Antibodies that bind to the gag-derived protein are then added. The solid phase is washed to removed unbound material. A control assay is performed in an identical manner except that no test compound is used. Detection of the antibodies that bind to the gag-derived protein indicates that the vpr and gag-derived proteins are capable of binding to each other in the presence of the test compound. Accordingly, failure to detect that antibodies that bind to vpr protein indicates that the test compound inhibits binding of vpr and gag-derived proteins. Quantifying the level of binding in the presence and absence of test compound allows for the measurement of the extent of modulation that the test compound can cause on vpr binding to a gag-derived protein.

In some preferred embodiments, antibodies that bind to the gag-derived protein are fixed to a solid phase. gag-derived protein is contacted with the fixed antibody to form a complex. The complex is contacted with vpr protein in the presence of a test compound. Anti-vpr antibodies are then added. The solid phase is washed to removed unbound material. A control assay is performed in an identical manner except that no test compound is used. Detection of the antibodies that bind to vpr protein indicates that the vpr and gag-derived proteins are capable of binding to each other in the presence of the test compound. Accordingly, failure to detect that antibodies that bind to vpr protein indicates that the test compound inhibits binding of vpr and gag-derived proteins. Quantifying the level of binding in the presence and absence of test compound allows for the measurement of the extent of modulation that the test compound can cause on vpr binding to a gag-derived protein.

In the methods of identifying compounds that inhibit vpr protein binding to a gag-derived protein, fragments of vpr may be used provided the fragment used retains its ability to bind to the gag-derived protein. Similarly, fragments of gag-derived proteins may be used provided the fragment used retains its ability to bind to vpr protein.

A further aspect of the present invention relates to kits for practicing the above described method of identifying compounds which inhibit vpr protein binding to a gag-derived protein. Kits according to this aspect of the invention comprises the a first container comprising vpr protein, a second container comprising a gag-derived protein. Additionally, to practice the above defined method, means are required to distinguish vpr protein bound to the gag-derived protein from unbound vpr protein or unbound gag-derived protein. In a preferred embodiment of this aspect of the invention, a third container comprising an antibody that specifically binds to either the vpr protein or a gag-derived protein is provided. At least one of the contained components, preferably the antibody, may be conjugated with an agent, such as those described above, which allows its presence to be detected. In another preferred embodiment of this aspect of the invention, a fourth container is provided which contains an antibody that specifically binds to either the vpr protein or a gag-derived protein, but not the protein which is bound by the antibody in the third container. At least one of the contained components, preferably the antibody, may be conjugated with an agent, such as those described above, which allows its presence to be detected. In the kits of the invention which are useful to practice the methods of identifying compounds that inhibit vpr protein binding to a gag-derived protein, fragments of vpr may be included provided the fragment used retains its ability to bind to the gag-derived protein. Similarly, fragments of gag-derived proteins may be included provided the fragment used retains its ability to bind to vpr protein.

It has also been discovered that the gag-derived protein, p24 binds to the gag-derived proteins, p15 and p6. Accordingly, additional aspects of the present invention involve methods of identifying compounds that inhibit p24 from binding to p15 and methods of identifying compounds that inhibit p24 from binding to p6. Furthermore, the present invention relates to kits for practicing methods of identifying compounds that inhibit p24 from binding to p15 and kits for practicing methods of identifying compounds that inhibit p24 from binding to p6. The methods and kits for practicing these methods are the same as those described above involving methods of identifying compounds that inhibit vpr from binding to gag-derived proteins except the proteins and fragments of proteins are p24 and p15 or p6 instead of vpr and the other gag-derived proteins and fragments thereof. Thus, the disclosure provided above is meant to include methods of identifying compounds that inhibit p24 from binding to p15 or p6 and kits for practicing such methods in which p24 and p15 or p6 are substituted for vpr and other gag-derived proteins as described above.

HIV assembly includes the aggregation of p24 molecules. The initiator of this aggregation is unknown. However, it has been discovered that an antibody, Mab 1238, induces the aggregation of p24 in vitro. It has also been found that p15, but not p7, also induces the aggregation of p24 in vitro. Because p15 is cleaved into p7 and p6, and p15 but not p7 induces the aggregation of p24, it is thought that p6 may play a major role in p24 aggregation. Thus, p15- or Mab 1238- induced p24 aggregation may be utilized to screen for particular compounds which may disrupt p24 aggregation and subsequent HIV particle assembly. This procedure would be an extremely significant assay for screening potential therapeutic compounds for HIV therapy.

Accordingly, another aspect of the present invention arises out of the discovery that p24 aggregation can be initiated by the presence of p15 or Mab 1238. The present invention relates to a method of identifying compounds which inhibit p24 aggregation which comprises the steps of maintaining p24 protein under conditions which promote its aggregation in the presence of a test compound, determining the level of p24 aggregation and comparing that level to the level of aggregation that occurs when p24 protein is maintained under the same conditions in the absence of a test compound. According to some embodiments, conditions which promote p24 aggregation include the presence of p15 or a monoclonal antibody 1238. The present invention relates to a kit for identifying compounds which inhibit p24 aggregation which comprises a first container comprising p24 protein and a second container comprising p15 protein or Mab 1238.

According to this aspect of the invention, a method is provided by which particular compositions can be examined to determine if they can inhibit p24 aggregation. The invention provides a method in which test compounds are added to p24 in vitro. Addition of p15 or Mab 1238 induces aggregation of p24 in the absence of the test compound. Addition of p15 or Mab1238 to p24 in the presence of test compound and subsequent examination of p24 aggregation by detecting p24 complexes allows for the identification of compounds which modulate p24 aggregation. Since p24 aggregation is essential to viral assembly of HIV, such compounds are useful as anti-HIV compounds.

The method of identifying compounds that inhibit p24 aggregation in vitro can be performed by those having ordinary skill in the art routinely using readily available starting materials. Mab 1238, p15 and p24 are all available and can be combined in concentrations to allow for detection of p24 aggregation without undue experimentation. Test compound is provided, preferably in solution. Serial dilutions of test compounds may be used in a series of assays. Test compound may be added at concentrations from 0.01

μM to 1 M. A preferred range of final concentrations of a test compound is from 10 μM to 100 μM. Means to visualize or otherwise detect p24 aggregation are routine. An α-helical peptide has been identified which is useful to inhibit induced p24 aggregation. The α-helical peptide spans gag amino acids 193–208.

Another aspect of the invention provides a composition that inhibits p24 aggregation. This composition comprises a 17-mer alpha-helical peptide.

Another aspect of the invention provides a kit useful to identify compound that modulate p24 aggregation. The kits may comprise a first container that contains p24, a second container that contains a p24 aggregation inducing compound such as p15 or Mab 1238. In some embodiments, a means to visualize p24 aggregation is provided. Such means may include a third container that contains a detectable antibody that binds to p24 and thus allows for aggregation to be detected. In some embodiments, a control is provided which comprises a container that contains the 17-mer alpha-helical peptide known to inhibit aggregation.

One skilled in the art will readily recognize the multitude of assays by which to p24 aggregation may be observed. Applicants have also discovered that p24 may be induced to aggregate. Both p15 and Mab 1238 have been observed to induce the aggregation of p24 in vitro. An assay by which to examine the induction of p24 aggregation comprises contacting p24 with a particular compound and determining the level of p24 aggregation with anti-p24 antibodies. It has been discovered that Mab 1238- or p15-induced p24 aggregation may be inhibited. An assay by which to examine the inhibition of p24 aggregation comprises contacting p24 with either p15 or Mab 1238 in the presence of a particular compound and determining the level of p24 aggregation with anti-p24 antibodies. To this end, a 17-mer peptide which interacts with the α-helix region of p24 has been found to block Mab 1238-induced p24 aggregation.

Presently, diagnostic tests that detect the presence of antibodies to HIV proteins, especially p24, in test samples from individuals suspected of being HIV+ often yield false results. Therefore, there is a great need to develop diagnostic tests by which to detect the presence of antibodies to additional HIV proteins, which will corroborate those results obtained from diagnostic tests that are currently available. In addition, antibodies to HIV proteins, especially p24, may not even be detected in an individual infected with HIV for a period of months after infection. Therefore, there is further need to develop additional diagnostic tests to detect the presence of the virus, or viral proteins, immediately after infection.

The vpr gene is found in all of the primate immunodeficiency viruses, with the possible exception of $SIV_{AGM}$. Vpr is an integral protein associated with the core and capsid of the retrovirus and is incorporated into the HIV particle in multiple copies. It has been discovered that vpr binds to gag-derived proteins (p55, p24, p15, p7 and p6) which allows for the packaging of vpr within the viral particle upon viral particle assembly. p24 gag protein is found free in the serum of HIV+ individuals at certain stages of infection as a result of virus disintegration in vivo. Detection of vpr and anti-vpr antibodies provides an alternative diagnostic to assess whether an individual has been infected with HIV. In addition, the quantity of vpr and anti-vpr antibodies may be a good prognosticator regarding the stage of disease.

The present invention relates to a diagnostic test in which the presence and/or amount of vpr in a test sample is determined. The present invention provides anti-vpr antibodies that recognize eukaryotically-produced vpr and offers an increased sensitivity for detection of vpr compared to the antibodies that are presently available, which recognize vpr produced in prokaryotic systems such as E. coli. These currently available antibodies only recognize vpr in approximately 30% of HIV+ patients. However, the antibodies of the present invention recognize vpr in approximately 80% of HIV+ patients, a dramatic increase in sensitivity. The presence of vpr in a test sample from an individual may also be an excellent indicator of HIV infection.

The present invention relates to methods of identifying individuals exposed to HIV by detecting presence of vpr protein in sample using antibodies which were produced in response to exposure to vpr protein produced in eukaryotic cells; i.e. anti-eukaryotically produced vpr. Specifically, it has been discovered that antibodies raised against eukaryotically produced vpr cross-reacts with vpr in samples from HIV infected individuals at a higher rate than prokaryotically produced vpr. The antibodies are preferably monoclonal antibodies. The antibodies are preferably raised against vpr made in human cells, CHO cells, insect cells or yeast cells. Quantification of the amount of vpr protein present in a sample of an individual may be used in determining the prognosis of an infected individual as the level of vpr in an infected individual may be indicative of the progress of infection.

The present invention relates to antibodies which are produced in response to exposure to vpr protein produced in eukaryotic cells. The antibodies are preferably monoclonal antibodies. The antibodies are preferably raised against vpr made in human cells, CHO cells, insect cells or yeast cells.

The present invention relates to kits for identifying individuals exposed to HIV comprising a first container which contains antibodies which were produced in response to exposure to vpr protein produced in eukaryotic cells and a second container which contains vpr protein produced in eukaryotic cells. The antibodies are preferably monoclonal antibodies. The antibodies are preferably raised against vpr made in human cells, CHO cells, insect cells or yeast cells. The vpr is preferably made in human cells, CHO cells, insect cells or yeast cells. The kits may be adapted for quantifying of the amount of vpr protein present in a sample of an individual. Such information may be used in determining the prognosis of an infected individual as the level of vpr in an infected individual may be indicative of the progress of infection.

Another aspect of the invention is a diagnostic test in which the presence and/or amount of anti-vpr antibodies in a test sample is determined. Previous reports have demonstrated anti-vpr reactivity in a subset of HIV+ individuals. Gras-Masse, H. et al. (1990) *Int. J. Pept. Protein Res.* 36:219; Reiss, P. et al. (1990) *J. Acquir. Immune Defic. Syndr.* 3:115; and Wong-Staal, F. et al. (1987) *AIDS Res. Hum. Retrovir.* 3:33. These studies demonstrated that between 25% and 49% of HIV+ individuals produce antibodies that bind to chemically synthesized and bacterially produced vpr, respectively. Thus, using prokaryotically-produced vpr to screen individuals for the presence of anti-vpr antibodies will only identify approximately one-half of the HIV population at best. The present invention provides a screen for anti-vpr antibodies using eukaryotically-produced vpr. In the diagnostic method of the present invention, 100% of anti-p24 antibody positive individuals display anti-vpr reactivity. The presence of anti-vpr antibodies in a test sample from an individual is an indicator of HIV infection.

The present invention relates to methods of identifying individuals exposed to HIV by detecting presence of antibodies against vpr protein in sample using vpr protein produced in eukaryotic cells. The vpr is preferably produced in human cells, CHO cells, insect cells or yeast cells. Quantification of the amount of anti-vpr antibodies present in a sample of an individual may be used in determining the prognosis of an infected individual as the level of anti-vpr antibodies in an infected individual may be indicative of the progress of infection.

The present invention relates to vpr protein produced in eukaryotic cells. The vpr is preferably produced in human cells, CHO cells, insect cells or yeast cells.

The present invention relates to kits for identifying individuals exposed to HIV comprising a first container which contains antibodies which were produced in response to exposure to vpr protein produced in eukaryotic cells and a second container which contains vpr protein produced in eukaryotic cells. The vpr is preferably produced in human cells, CHO cells, insect cells or yeast cells. The antibodies are preferably raised against vpr made in human cells, CHO cells, insect cells or yeast cells. The kits may be adapted for quantifying the amount of anti-vpr antibodies present in a sample of an individual. Such information may be used in determining the prognosis of an infected individual as the level of anti-vpr antibodies in an infected individual may be indicative of the progress of infection.

Kits for the detection of vpr and anti-vpr antibodies are useful for research as well as diagnostic and prognostic purposes.

The means to detect the presence of a protein or an antibody in a test sample are routine and one having ordinary skill in the art can detect the presence or absence of a protein or an antibody using well known methods. One well known method of detecting the presence of a protein or an antibody is in a binding assay. One having ordinary skill in the art can readily appreciate the multitude of ways to practice a binding assay to detect the presence of a protein or an antibody. For example, antibodies are useful for immunoassays which detect or quantitate a specific protein. Antigens are useful for immunoassays which detect or quantitate a specific antibody. Some immunoassays comprise allowing proteins in the test sample to bind a solid phase support or to antibodies fixed to a solid phase. Detectable antibodies are then added which selectively binding to either the protein of interest or the uncomplexed antibody. Detection of the detectable antibody indicates the presence of the protein of interest if the detectable antibody is specific for the protein or the absence of the protein of interest if the detectable antibody is specific for uncomplexed antibody. Some immunoassays comprise allowing antibodies in the test sample to bind to an antigen that is fixed to a solid phase support and detecting the antigen/antibody complex using a detectable antibody which binds to either the antibody of interest or the antigen. Various immunoassay procedures are described in Immunoassays for the 80's, A. Voller et al., Eds., University Park, 1981.

Simple binding assays may be performed in which a solid phase support is contacted with the test sample. Any proteins present in the test sample bind the solid phase support and can be detected by a specific, detectable antibody preparation. Such a technique is the essence of the dot blot, Western blot and other such similar assays. The presence of specific antibodies in a test sample may also be detected in a similar manner. A target protein, to which the specific antibody binds, is contacted with the test sample and the subsequent binding to antibodies, if present in the test sample, is analyzed by a variety of methods known to those skilled in the art. Any antibodies present in the test sample bind the solid phase support and can be detected by detectable antigen or a specific, detectable antibody preparation.

Other immunoassays may be more complicated but actually provide excellent results. Typical and preferred immunometric assays include "forward" assays for the detection of a protein in which a first anti-protein antibody bound to a solid phase support is contacted with the test sample. After a suitable incubation period, the solid phase support is washed to remove unbound protein. A second, distinct anti-protein antibody is then added which is specific for a portion of the specific protein not recognized by the first antibody. The second antibody is preferably detectable. After a second incubation period to permit the detectable antibody to complex with the specific protein bound to the solid phase support through the first antibody, the solid phase support is washed a second time to remove the unbound detectable antibody. Alternatively, the second antibody may not be detectable. In this case, a third detectable antibody, which binds the second antibody is added to the system. This type of "forward sandwich" assay may be a simple yes/no assay to determine whether binding has occurred or may be made quantitative by comparing the amount of detectable antibody with that obtained in a control. Such "two-site" or "sandwich" assays are described by Wide, *Radioimmune Assay Method*, Kirkham, Ed., E. & S. Livingstone, Edinburgh, 1970, pp. 199–206.

The "forward" assay may also be adapted for the detection of antibodies that may be present in a test sample, henceforth referred to as "sample antibodies". The specific target protein to which the sample antibodies bind is bound to the solid phase support and contacted with the test sample. After a suitable incubation period, the solid phase support is washed to remove unbound sample antibodies. A first antibody that binds to the Fc portion of the sample antibodies is added. This first antibody is preferably detectable. Alternative, in the case where the first antibody is not detectable, a second detectable antibody which binds the first antibody must be used to detect the binding. After a second incubation period to permit the detectable antibody to complex with the sample antibody bound to the target protein/solid phase support, the solid phase support is washed a second time to remove the unbound detectable antibody. This type of "forward sandwich" assay may also be a simple yes/no assay to determine whether binding has occurred or may be made quantitative by comparing the measure of detectable antibody with that obtained in a control.

Other types of immunometric assays are the so-called "simultaneous" and "reverse" assays. A simultaneous assay involves a single incubation step wherein the first antibody bound to the solid phase support, the second, detectable antibody and the test sample are added at the same time. After the incubation is completed, the solid phase support is washed to remove unbound proteins. The presence of detectable antibody associated with the solid support is then determined as it would be in a conventional "forward sandwich" assay. The simultaneous assay may also be adapted in a similar manner for the detection of antibodies in a test sample.

The "reverse" assay comprises the stepwise addition of a solution of detectable antibody to the test sample followed by an incubation period and the addition of antibody bound to a solid phase support after an additional incubation period. The solid phase support is washed in conventional fashion to remove unbound protein/antibody complexes and unreacted detectable antibody. The determination of detectable antibody associated with the solid phase support is then determined as in the "simultaneous" and "forward" assays. The reverse assay may also be adapted in a similar manner for the detection of antibodies in a test sample.

The first component of the immunometric assay may be added to nitrocellulose or other solid phase support which is capable of immobilizing proteins. The first component for determining the presence of vpr in a test sample is anti-vpr antibody, whereas the first component for examining for the presence of anti-vpr antibodies in a test sample is eukaryotically-produced vpr. By "solid phase support" or "support" is intended any material capable of binding proteins. Well-known solid phase supports include glass, polystyrene, polypropylene, polyethylene, dextran, nylon, amylases, natural and modified celluloses, polyacrylamides, agaroses, and magnetite. The nature of the support can be either soluble to some extent or insoluble for the purposes of the present invention. The support configuration may be spherical, as in a bead, or cylindrical, as in the inside surface of a test tube or the external surface of a rod. Alternatively, the surface may be flat such as a sheet, test strip, etc. Those skilled in the art will know many other suitable "solid phase supports" for binding proteins or will be able to ascertain the same by use of routine experimentation. A preferred solid phase support is a 96-well microtiter plate.

To detect the presence of a protein, in this case either vpr or anti-vpr antibodies, detectable antibodies, such as anti-vpr antibodies or anti-human antibodies, are used. Several methods are well known for the detection of antibodies.

One method in which the antibodies can be detectably labeled is by linking the antibodies to an enzyme and subsequently using the antibodies in an enzyme immunoassay (EIA) or enzyme-linked immunosorbent assay (ELISA), such as a capture ELISA. The enzyme, when subsequently exposed to its substrate, reacts with the substrate and generates a chemical moiety which can be detected, for example, by spectrophotometric, fluorometric or visual means. Enzymes which can be used to detectably label antibodies include, but are not limited to malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. One skilled in the art would readily recognize other enzymes which may also be used.

Another method in which antibodies can be detectably labeled is through radioactive isotopes and subsequent use in a radioimmunoassay (RIA) (see, for example, Work, T. S. et al., *Laboratory Techniques and Biochemistry in Molecular Biology*, North Holland Publishing Company, N.Y., 1978). The radioactive isotope can be detected by such means as the use of a gamma counter or a scintillation counter or by autoradiography. Isotopes which are particularly useful for the purpose of the present invention are $^3H$, $^{125}I$, $^{131}I$, $^{35}S$, and $^{14}C$. Preferably $^{125}I$ is the isotope. One skilled in the art would readily recognize other radioisotopes which may also be used.

It is also possible to label the antibody with a fluorescent compound. When the fluorescent-labeled antibody is exposed to light of the proper wave length, its presence can be detected due to its fluorescence. Among the most commonly used fluorescent labeling compounds are fluorescein isothiocyanate, rhodamine, phycoerythrin, phycocyanin, allophycocyanin, o-phthaldehyde and fluorescamine. One skilled in the art would readily recognize other fluorescent compounds which may also be used.

Antibodies can also be detectably labeled using fluorescence-emitting metals such as $^{152}Eu$, or others of the lanthanide series. These metals can be attached to the protein-specific antibody using such metal chelating groups as diethylenetriaminepentaacetic acid (DTPA) or ethylenediamine-tetraacetic acid (EDTA). One skilled in the art would readily recognize other fluorescence-emitting metals as well as other metal chelating groups which may also be used.

Antibody can also be detectably labeled by coupling to a chemiluminescent compound. The presence of the chemiluminescent-labeled antibody is determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester. One skilled in the art would readily recognize other chemiluminescent compounds which may also be used.

Likewise, a bioluminescent compound may be used to label antibodies. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin. One skilled in the art would readily recognize other bioluminescent compounds which may also be used.

Detection of the protein-specific antibody, fragment or derivative may be accomplished by a scintillation counter if, for example, the detectable label is a radioactive gamma emitter. Alternatively, detection may be accomplished by a fluorometer if, for example, the label is a fluorescent material. In the case of an enzyme label, the detection can be accomplished by colorometric methods which employ a substrate for the enzyme. Detection may also be accomplished by visual comparison of the extent of enzymatic reaction of a substrate in comparison with similarly prepared standards. One skilled in the art would readily recognize other appropriate methods of detection which may also be used.

The binding activity of a given lot of antibodies may be determined according to well known methods. Those skilled in the art will be able to determine operative and optimal assay conditions for each determination by employing routine experimentation.

Positive and negative controls may be performed in which known amounts of protein and no protein, respectively, are added to the assay. One skilled in the art would have the necessary knowledge to perform the appropriate controls. To determine the quantity of vpr or anti-vpr antibodies in a test sample, the amount of protein detected in the test sample is compared to the amount of protein detected in the positive control. A standard curve is generated from the positive control values and the amount of protein in the test sample is extrapolated from said standard curve. One skilled in the art would have the knowledge to construct a standard curve and extrapolate the value of the test sample.

Eukaryotically-produced vpr includes vpr produced in mammalian or viral expression systems, as opposed to vpr produced in prokaryotes, such as in *E. coli*. A viral expression system, such as baculovirus, is preferred. One skilled in the art would appreciate the different eukaryotic expression systems with which vpr may be produced.

Test samples include those samples that are obtained from individuals suspected of being HIV and may consist of blood, cerebral spinal fluid, amniotic fluid, lymph, semen, vaginal fluid or other body fluids. Test samples also include those samples prepared in the laboratory, such as those used for research purposes. Cells, if present, may be removed by methods such as centrifugation or lysis. One skilled in the art would readily appreciate the variety of test samples that may be examined for vpr and anti-vpr antibodies. Test samples may be obtained by such methods as withdrawing fluid with a needle or by a swab. One skilled in the art would readily recognize other methods of obtaining test samples.

An "antibody composition" refers to the antibody or antibodies required for the detection of the protein. For example, the antibody composition used for the detection of vpr in a test sample comprises a first antibody that binds eukaryotically-produced vpr as well as a second or third detectable antibody that binds the first or second antibody, respectively.

To examine a test sample for the presence of anti-vpr antibodies, a standard immunometric assay may be performed. 10–50 µg/ml of eukaryotically-produced vpr is added to a solid phase support, such as a 96-well microtiter plate, in a volume of buffer. 50 µl/ml are added per well. The solid phase support is incubated for a period of time sufficient for binding to occur and subsequently washed with PBS to remove unbound vpr. Examples of appropriate conditions are 2 hours at room temperature or 4° overnight. The solid phase support is then blocked with a PBS/BSA solution to prevent proteins in the test sample from nonspecifically binding the solid phase support. Serial dilutions of test sample are added to the solid phase support which is subsequently incubated for a period of time sufficient for binding to occur. The solid phase support is washed with PBS to remove unbound protein. Labeled anti-human antibodies, which recognize the Fc region of human antibodies, are added to the solid phase support mixture. The plate is incubated for a period of time sufficient for binding to occur and subsequently washed with PBS to remove unbound labeled anti-human antibody. The amount of labeled and bound anti-human antibodies is subsequently determined by standard techniques. The anti-human antoibodies that may be used include goat anti-human, horse radish peroxidase labelled (Boehringer Mannheim)used at 1:12000 according to manufacturers directions.

To examine a test sample for the presence of vpr, a standard immunometric assay such as the one described below may be performed. A first anti-vpr antibody, which recognizes a specific portion of eukaryotically-produced vpr, is added to a 96-well microtiter plate in a volume of buffer. The plate is incubated for a period of time sufficient for binding to occur and subsequently washed with PBS to remove unbound anti-vpr antibody. The plate is then blocked with a PBS/BSA solution to prevent sample proteins from nonspecifically binding the microtiter plate. Serial dilutions of test sample are subsequently added to the wells and the plate is incubated for a period of time sufficient for binding to occur. The wells are washed with PBS to remove unbound protein. Labeled anti-vpr antibodies, which recognize portions of eukaryotically-produced vpr not recognized by the first anti-vpr antibody, are added to the wells. The plate is incubated for a period of time sufficient for binding to occur and subsequently washed with PBS to remove unbound, labeled anti-vpr antibody. The amount of labeled and bound anti-vpr antibody is subsequently determined by standard techniques. A rabbit anti-vpr antibody that recognizes vpr amino acids 2–21 (#808) used at 1:1000. Examples of appropriate conditions are 2 hours at room temperature or 4° overnight.

Vpr kits, which are useful for the detection of vpr in a test sample, comprise solid support, positive and negative controls, buffer, appropriate anti-vpr antibodies and instructions for carrying out the capture ELISA assay essentially as previously described. Anti-vpr kits, which are useful for the detection of anti-vpr antibodies in a test sample, comprise solid support, positive and negative controls, buffer, eukaryotically-produced vpr and instructions for carrying out the capture ELISA assay essentially as previously described.

It has been discovered that vpr enhances HIV expression by as much as 100- to 1000-fold and this increased expression lasts for as long as one week. Thus, vpr may be used to increase the sensitivity of detection of HIV, and possibly other retroviruses, in a quantitative virus load assay. In addition, potential therapeutic agents for HIV may be screened for their anti-growth effects by examining their ability to inhibit vpr-induced HIV expression.

The present invention relates to methods of increasing the sensitivity of detection of HIV and other retroviruses in a quantitative virus load assay by including a step in the assay which comprises adding vpr. Since vpr enhances viral replication, the viral load assays results will be exaggerated and therefore more sensitive. Viral load assays measure the amount of virus present. Fir example, plaque assays can count the number of viral particles per a fixed amount of serum. Other viral load assays are equally well known. One having ordinary skill in the art can readily adapt well known viral load assays to increase sensitivity by addition of vpr. The addition of vpr to a plaque assay, for example results in a faster generation of plaques and thereby reduces the amount of time needed to compile data and determine viral load. In infection assays, the addition of vpr to permissive cells and a sample will increase the infectability of the cells and result in the ability to detect the presence of infection particles more quickly and with greater sensitivity. Cells transformed with DNA that encodes vpr may be used in viral load assays rather that addition of vpr protein.

Another aspect of the invention is a method of examining potential inhibitors of vpr. The present invention provides such a method wherein compounds are examined for their ability to reduce vpr-enhanced retroviral growth. The rate of growth is then compared to vpr-induced retroviral growth in the absence of any such compounds.

Another aspect of the invention is a kit by which to examine the ability of a compound to inhibit vpr-induced retroviral growth.

Another aspect of the invention is a method of enhancing retroviral replication in vitro. The present invention provides such a method wherein in vitro retrovirus production is increased in order to increase yields of virus. The production of virus for research purposes may thereby be increases. vpr in incorporated into replication protocols as a reagent. Alternatively, cells transformed with DNA encoding vpr are used as hosts for retrovirus replication procedures, such cells providing higher yields than non-transformed cells.

Retroviral growth may be examined by culturing susceptible cells in vitro in the presence of a specific retrovirus. Susceptible cells may be cultured in conventional tissue culture flasks, petri plates or other material known to those skilled in the art. Cells and retrovirus may be suspended in conventional media such as RPMI or Hank's Balanced Salt Solution or other such media as known to those skilled in the art.

Susceptible cells are defined by their ability to be infected by retroviruses. Said cells support the replication of retroviruses in vitro. Examples of susceptible cells include but are not limited to HL60, SupT-1, THP-1, KG-1, U937, H9, OM-10.1, U1.1, LL58 and ACH-2 cells. One skilled in the art will readily recognize the variety of cells capable of being infected with a retrovirus.

Retroviruses comprise a class of viruses which contain RNA rather than DNA as their genetic material. Retroviruses include but are not limited to human immunodeficiency viruses (HIV), simian immunodeficiency viruses (SIV), avian leukemia viruses (ALV), murine leukemia viruses (MLV), mouse mammary tumor viruses (MMTV), avian sarcoma viruses (ASV), murine sarcoma viruses (MSV), feline sarcoma viruses (FSV), simian sarcoma viruses (SSV) and human T cell leukemia viruses (HTLV). One skilled in the art would readily recognize other examples of retroviruses as well as various strains of each that would function in the invention as described herein.

Retroviral growth may be measured at any time post-infection with the retrovirus by determining the titer of the retrovirus in the tissue culture supernatant. One skilled in the art will readily appreciate the multitude of methods by which the titer of a virus can be measured. A capture ELISA, as described previously, in which p24 is detected is preferred. One skilled in the art will readily recognize that the titer of virus may be determined by antibodies to other retroviral proteins depending upon the retrovirus with which the cells are infected.

Retroviral growth may be enhanced by culturing retroviral-infected cells in the presence of eukaryotically-produced vpr. Eukaryotically-produced vpr has been described previously. Eukaryotically-produced vpr may be obtained as a supernatant from cells infected with vpr baculovirus expression vector or as a purified or partially purified preparation. Baculovirus supernatant containing vpr may be added to the cells at a 0.01% to an undiluted concentration. Control supernatants comprise those supernatants from uninfected cells or from cells infected with baculovirus expression vectors which do not contain vpr constructs. Vpr may be added at any time during culture of the cells, preferably within 14 days before infection with retrovirus, more preferably within 9 days before infection with retrovirus. vpr camn be added at any time and may be kept in ocntact with cells for as little as 2 minutes to 3 hours.

The effects of exogenous vpr on HIV infection of monocyte and T cell lines in vitro have been examined. When added at the time of infection, vpr increased the rate of virus production in all cell lines examined, in a dose-dependent manner, for at least three weeks following a single exposure to vpr. An increase in viral titer of 100-fold over control was typical by day 5–8, and increases exceeding 1000-fold were observed in some experiments. Growth of HIV strains with monotropic phenotype (Ba-L) and lymphotropic phenotype (NL43) were enhanced by vpr in both lymphoid and myeloid lines. Vpr increased HIV expression from cell lines whose proliferation is either inhibited by vpr (THP-1, U937, KG-1, SupT-1, H9) or enhanced by vpr (HL60). The outcome of infection of the non-vpr treated cells varied from experiment to experiment. In some cases control cells failed to become productively infected, while in others, measurable virus production ceased after several days. In contrast, infection of vpr treated cells uniformly resulted in productive infection.

In other experiments, OM-10.1 cells, which are T lymphoid in origin, were treated with either control supernatant lacking vpr or vpr supernatant from baculovirus-infected cells. Cells are shown in visible light and stained for intracellular p24 detected by fluorescence microscopy. The intensity of fluorescence is a measure of the virus expression. Thus, addition of exogenous vpr induces a high level of retrovirus expression.

Vpr-depleted supernatants showed little activity in the infection assay. In other experiments, rabbit anti-vpr peptide serum dramatically decreased vpr enhancement of retroviral growth and rabbit anti-vpr polyclonal serum completely eliminated it, while normal rabbit serum (NRS) had no effect. The anti-vpr serum did not influence virus production in non-vpr cultures nor virus expression from chronically infected, high producing cell lines.

Adherence-selected peripheral blood macrophages and adherence-depleted, PHA-stimulated normal peripheral blood lymphocytes from a healthy, HIV-negative donor were treated with vpr and infected with either the monotropic (Ba-L) or lymphotropic (NL43) strain of HIV, respectively. In each case, vpr increased virus production up to 10-fold, indicating that vpr has similar effects on normal untransformed cells.

Cell lines that were exposed to vpr, then cultured in the absence of the agent for up to 9 days prior to infection, showed an increase in viral infection and replication similar to that of the cells treated at the time of infection. In one case the vpr-treated lines became productively infected while the control cells failed to do so. This is further evidence that the activity of vpr is directed at the target cells and that the vpr-induced alteration in cell status is a primary activity for vpr.

The present invention relates to a method of enhancing retroviral propagation in cell culture by contacting the cells with vpr protein in conjunction with infection of the cells by retrovirus. The vpr protein may be added before, after or simultaneously with the retrovirus.

The present invention relates to a method of enhancing retroviral propagation in cell culture by introducing into the cells a nucleic acid molecule that comprises a sequence that encodes vpr protein in conjunction with infection of the cells by retrovirus. The nucleic acid molecule that comprises a sequence that encodes vpr protein may be introduced into the cells before, after or simultaneously with the retrovirus.

The present invention relates to methods of identifying compounds which inhibit vpr's ability to enhance retroviral replication by infecting cells with a retrovirus in the presence of vpr protein and a test compound and comparing the amount of virus produced as a result of such infection to the amount of virus produced in an identical infection protocol except in the absence of test compound.

The present invention relates to methods of identifying compounds which inhibit vpr's ability to enhance retroviral replication by infecting cells that produce vpr protein with a retrovirus in the presence of vpr protein and a test compound and comparing the amount of virus produced as a result of such infection to the amount of virus produced in an identical infection protocol except in the absence of test compound. The cells comprise a nucleic acid molecule that comprises a sequence that encodes vpr protein.

The present invention relates to methods of modifying macrophage state of differentiation by contacting macrophage cells with vpr protein. It has been discovered that vpr induces changes in macrophage cells. Such a property can be used to induce changes in macrophage in individuals suffering from diseases and conditions in which macrophage cells are involved. Such diseases and conditions include autoimmune diseases and granulomas. By administering pharmaceutical compositions that comprise vpr protein or nucleic acid molecules that comprise sequences such as those described above following the regimens described above, the macrophage cells of the individual being treated can be induced to change states of differentiation. Such activity can lessen or eliminate the cause or symptoms of the disease or condition being treated.

The present invention relates to methods of treating individuals diagnosed with or suspected of suffering from diseases characterized by undesirable activity of macrophage cells. According to some embodiments, the method of the present invention comprises the steps of administering to such individuals, an effective amount of vpr protein or a functional fragment of vpr protein. According to some embodiments of the present invention, the method of the present invention comprises the steps of administering to such individuals, an effective amount of a nucleic acid molecule that comprises a sequence which encodes vpr protein or a functional fragment of vpr protein. According to some embodiments of the present invention, the sequence that encodes vpr protein or a functional fragment of vpr protein is operably linked to regulatory elements which are necessary for expression of the sequence in cells. According to some embodiments of the present invention, the nucleic acid molecule is DNA. According to some embodiments of the present invention, the disease characterized by undesirable activity of macrophage cells is an autoimmune disease or a granuloma.

Some aspects of the invention relate to pharmaceutical compositions, drug delivery systems and methods for specifically targeting vpr and other biologically active agents to specific cells. Viral particle comprising cell specific envelope proteins and p24 bound to vpr may be produced. Such particles will deliver vpr to the cells for which the envelope is specific. Vpr is thus delivered to cells which it then produces an effect upon. The present invention relates to compositions useful for delivering vpr into specifically targeted cells. The composition comprise vpr, p24 and a cell-type specific coat protein assembled as a particle which is a drug delivery particle that can specifically deliver vpr cells that the coat protein binds to. The present invention relates to the particles, to the pharmaceutical compositions that comprise the particles and pharmaceutically acceptable carriers, to the nucleic acid molecules that encode the components, to the expression vectors and host cells that contain the nucleic acid molecules and to the methods of producing and using the compositions.

To prepare a drug delivery particle of the invention, the envelope protein (env) of a retrovirus is chosen based upon the cell type such a retrovirus infects. Cell specific envelope proteins are well known. Cells are co-transfected with a nucleic acid molecule that encodes the desired env, a nucleic acid molecule that encodes vpr, a nucleic acid molecule that encodes p24 or a nucleic acid molecule that encodes the full length gag precursor plus the HIV protease. Expression of these sequences will result in the proteins thus encoded being produced and assembly of the drug delivery particle. Noncoding RNA may also be provided for safety since the assembling particle will package RNA.

The present invention relates to compositions useful for delivering fusion compounds into specifically targeted cells. The fusion compound comprises a biologically active portion and a vpr fragment which binds to p24. The compositions comprise the fusion compound, p24 and a cell-type specific coat protein assembled as a particle which is a drug delivery particle that can specifically deliver the fusion compound to cells that the coat protein binds to. The present invention relates to the fusion compounds, to the particles, to the pharmaceutical compositions that comprise the particles and pharmaceutically acceptable carriers, to the nucleic acid molecules that encode the components, to the expression vectors and host cells that contain the nucleic acid molecules and to the methods of producing and using the compositions.

To prepare a fusion drug delivery particle of the invention, the envelope protein (env) of a retrovirus is chosen based upon the cell type such a retrovirus infects. Cell specific envelope proteins are well known. A chimeric gene is designed which includes the portion of the vpr protein that binds to p24 together with a biological active protein which retains its activity when linked to the portion of vpr. Cells are co-transfected with a nucleic acid molecule that encodes the desired env, the chimeric gene, a nucleic acid molecule that encodes p24 or a nucleic acid molecule that encodes the full length gag precursor plus the HIV protease. Expression of these sequences will result in the proteins thus encoded being produced and assembly of the drug delivery particle. Noncoding RNA may also be provided for safety since the assembling particle will package RNA.

Biologically active proteins which can be used in fusion proteins include cytokines, lymphokines, structural proteins such as dystrophins, other therapeutic proteins and proteins which are useful as immune targets.

As an immunotherapeutic, the administration of vpr or an immunogenic fragment of vpr, particularly an inactive, i.e. non-functional, immunogenic fragment, provides a target against which an individuals immune system can mount an immune response which will recognize viral produced vpr and inactivate it. The vpr or fragment thereof is preferably eukaryotically produced. It is administered in a dose sufficient to evoke a protective immune response. Multiple doses may be administered. One having ordinary skill in the art can readily formulate an immunogenic composition that comprises vpr or fragment thereof. Adjuvants may be included in such formulations.

Alternatively, anti-vpr antibodies may be administered as therapeutics to treat individuals infected with HIV. The anti-vpr antibodies are preferably produced against eukaryotically-produced vpr. They are administered in an effective dose; i.e. a dose sufficient to inactivate some or all of the vpr present in the individual such that the progress of HIV in the individual is inhibited or otherwise reduced. Multiple doses may be administered. One having ordinary skill in the art can readily formulate anti-vpr antibodies and determine effective dosages.

The present invention relates to pharmaceutical compositions that comprise vpr protein and a pharmaceutically acceptable carrier which can be used as an HIV vaccine or immunotherapeutic. The present invention relates to pharmaceutical compositions that comprise immunogenic fragments of vpr protein and a pharmaceutically acceptable carrier which can be used as an HIV vaccine or immunotherapeutic. The immunogenic fragments are preferably inactive fragments. The present invention relates to pharmaceutical composition comprising anti-vpr antibodies and a pharmaceutically acceptable carrier which can be used as an HIV immunotherapeutic.

The present invention relates to a method of treating an individual exposed to HIV by administering an immunogenic amount of vpr. The present invention relates to a method of treating an individual exposed to HIV by administering an immunogenic amount of inactive immunogenic vpr fragment. The present invention relates to a method of treating an individual exposed to HIV by administering a therapeutically effective amount of anti-vpr antibodies.

While the portions of the disclosure herein which relate to therapeutic compositions and methods primarily relates to therapeutics and methods of treating humans, the compositions and methods of the present invention can be applied to veterinary medical uses as well. It is within the scope of the present invention to provide methods of treating non-human as well as human individuals. Accordingly, the present invention relates to a method of treating all animals, particularly mammalian species including human, bovine, ovine, porcine, equine, canine and feline species.

EXAMPLES

Example 1

Summary

The vpr gene of HIV-1 is sufficient for the differentiation of the human rhabdomyosarcoma cell line TE671, a cell lines from rhabdomyosarcomas, which are tumors of muscle origin and which can be induced to differentiate in vitro. Differentiated cells are characterized by great enlargement, altered morphology, lack of replication, and high level expression of the muscle-specific protein myosin. Morphological differentiation and inhibition of proliferation of two other transformed cell lines has also been observed. vpr-transfected cells remain fully viable in culture for extended periods.

The development of mature skeletal muscle cells entails an ordered process of cellular differentiation from muscle-committed mycocytes (presumptive myoblasts), to postmitotic myoblasts, to mature multinucleated myotubes possessing a functional muscle-contractile apparatus. Embryonal rhabdomyosarcoma is a cancer of cells resembling presumptive myoblasts and may originate from muscle satellite cells (Bruni, 1979). Rhabdomyosarcoma cell lines have been used in studies of muscle differentiation and tumorigenesis, and they can be induced to differentiate from a rapidly dividing population of cells (myoblast-like) that express low amounts of a few mature-muscle proteins to postmitotic, greatly enlarged and elongated, multinucleated (myotube-like) cells that express high amounts of mature-muscle-specific proteins and a functional muscle-contractile apparatus (Aguanno, S., et al., (1990) *Cancer Res.* 50:3377–3382; Hiti, A. L., et al., (1989) *Mol. Cell. Biol.* 9:4722–4730; Siegel, H. N., and Lukas, R. J. (1988) *Dev. Brain Res.* 44:269–280; and Stratton, M. R., et al., (1989) *Carcinogenesis* 10:899–905.)

HIV expression in a human muscle cell tumor line leads to inhibition of proliferation and activation of the suppressed endogenous cell differentiation program. The vpr gene of HIV-1 is sufficient for the observed effects and necessary for differentiation of essentially all cells. These results establish HIV-1 vpr as a regulatory protein capable of profound regulation of cell functions, including cell proliferation and differentiation.

Experimental Procedures

Cell Lines and Cultivation

The human embryonal rhabdomyosarcoma TE671 line (ATCC HTB 139) and the canine osteosarcoma D17 line (ATCC CLL 183) were obtained from the American Type Culture Collection, Rockville, Md. TE671 was originally classified as a medulloblastoma line. RD cells were provided by Dr. A. Srinivasan. All cells were grown in Dulbecco's modified Eagle's medium supplemented with 10% fetal calf serum, penicillin-streptomycin, and sodium pyruvate and maintained in a 5%–6% $CO_2$ atmosphere at 37° C.

Construction of the TE671Ψ Cell Line

TE671 cells were infected with replication-defective murine retrovirus containing the human CD4 retroviral expression vector T4-pMV7 as described in Weiner, D. B., et al., (1991). *Pathobiology* 59:361–371. Clonal populations were analyzed for CD4 expression by flow cytometry as described in Weiner, D. B., et al., (1989) *Oncogene* 4:1175–1183. Briefly, cells were incubated with either Leu-3a, a murine monoclonal antibody specific for the human CD4 cell surface molecule, or Upc-21, an irrelevant isotype-matched murine monoclonal antibody. Secondary antibody was a fluorescein-labeled goat anti-mouse antibody. A stable $CD4^+$ clone was selected for further analysis and designed TE671Ψ

Plasmids and Cloning Strategies

The HIV-1 genomic clone pNL43 was obtained through the National Institutes of Health (NIH) AIDS Research and Reference Reagent Program, Division of AIDS, National Institute of Allergy and Infectious Diseases, NIH, (Adachi, A., et al. (1986) *J. Virol.* 59:284–291), and was used as the starting material for most of the genetic constructs used in this study. The pNL43 plasmid consists of HIV-1 proviral DNA plus 3 kb of host sequence from the site of integration cloned into pUC18.

Construction of pNLpuro

To simplify further cloning steps, the StuI site within the non-HIV 5' flanking human DNA of pNL43 was destroyed by partial digestion with StuI followed by digestion of the free ends with *Escherichia coli* polymerase. The linear plasmid was filled, then self-ligated, leaving a unique StuI site within the HIV genome. This plasmid, pNLΔstu, was then digested with the blunting enzymes StuI and BsaBI, which eliminated a large section of the coding sequence for gp120. The SV40 promoter and puromycin resistance coding region (puromycin acetyltransferase) were isolated from pBABE-puro (Morganstern, J. P., and Land, H. (1990). *Nucl. Acids Res.* 18:3587–3596; kindly provided by Dr. Hartmut Land of the Imperial Cancer Research Fund) using EcoRl and Clal This fragment was blunted, then cloned into the StuI-BsaBI-digested pNLΔstu. A clone was selected with the SV40-puro fragment in the correct orientation so that the 3' long terminal repeat of HIV could provide poly(A) functions for the puromycin acetyltransferase message. This plasmid was designated pNLpuro.

HIV-1 Regulatory Genes

DNA encoding HIV-1 vpr protein was amplified via PCR from the HIV-1 genomic plasmid pNL43. PCR was performed under conditions that yield DNA amplification with highly fidelity (Ling, L. L., et al., (1991) *PCR Meth. Appl.* 1:63–69). Three PCR primers were used to amplify the gene. One primer, called a universal start/cloning primer (USP), encodes appropriate restriction sites for cloning the PCR product into a vector, a consensus sequence determined by Kozak, M. (1986) *Cell* 44:283–292, to promote strong initiation of translation, and an ATG start site. This primer was used in the amplification of the gene. The USP was placed in a PCR with a second short primer consisting of a reverse complement of the 3' end of the USP plus approximately 15 bp of the 5' end of the vpr gene. The double-stranded product of this PCR was used as a 5' primer in a second reaction with an appropriate 3' primer specific for the gene of interest. The 3' primer introduced restriction sites for cloning the PCR product. The sequences of the primers are as follows:

USP:ggcggctcgaggatccgccgccaccatg (SEQ ID NO:1).

vpr primer: 5' linker primer, complementary to the USP and the vpr open reading frame 5' end: ggggcttgttccatggtggc (SEQ ID NO:2).

vpr primer: 3' cloning primer, complementary to the 3' end of the vpr open reading frame plus the BamHl cloning site: ccgcggatcctaggatctactggc (SEQ ID NO:3).

The resulting PCR product was cloned into the retroviral vector pBABE-puro. The vector pBabe-puro, which is used as a starting material to produce many of the below listed constructs, was originally constructed and reported by Morgenstern, J. P. and H. Land, 1990 Nucl. Acids Res. 18(12):3587–3596, which is incorporated herein by reference. The pBabe-puro plasmid is particularly useful for expression of exogenous genes in mammalian cells. DNA sequences to be expressed are inserted at cloning sites under the control of the Moloney murine leukemia virus (Mo MuLV) long terminal repeat (LTR) promoter. The plasmid contains the selectable marker for puromycin resistance. The resulting plasmid is designated pBabe-puro+vpr.

HIV regulatory genes nef, vpu and vif were amplified via PCR from the HIV-1 genomic plasmid pNL43. Primers designed to amplify the remaining regulatory genes (vif, vpu, nef) were constructed by the same design principle as employed in the amplification of vpr. Each gene was then cloned into pBabe-puro.

Cloning Strategy for Deletion of the vpr Gene from the HIV Genome

A region from just upstream of the unique PflMI site to just after the vif termination codon was amplified via PCR using primers that introduced a nonconservative amino acid change (Glu→Val) at amino acid 22 of vpr, a stop codon in the vpr reading frame immediately after amino acid 22, and an EcoRl site immediately following the new stop codon. This PCR fragment was substituted for the PflMl-EcoRl fragment of pNLpuro or pNL43. This substitution resulted in the deletion of 122 nt of the open reading frame of vpr, thus eliminating the possibility of reversion. The resulting plasmids, pNLpuroΔvpr and pNLΔvpr, encode the first 21 natural amino acids of vpr plus a valine plus all other remaining HIV-1 genes and splice junctions in their native form.

HIV-1 env-rev Plasmid

The region encoding the two exons of rev and the vpu and env open reading frames of HIV-1 HXB2 was amplified via PCR and cloned into the expression vector pCDNAl/neo (Invitrogen). Expression of rev and env proteins was demonstrated by Western blot analysis and by the ability of cells transfected with this construct to fuse with CD4$^+$ cell lines.

tat

HIV-1 tat expression plasmid pCV1 was obtained through the Aids Research and Reference Reagent Program. A region from the vector pBABE-hygro (Morganstern, J. P., and Land, H. (1990). Nucl. Acids Res. 18:3587–3596) expressing hygromycin resistance was subcloned into this plasmid to make pCV1-hygro. Alternatively, pCV1 was cotransfected with pBABE-puro at a ratio of 100:1. Identical results were obtained with both methods.

Determination of Regulatory Gene Expression by Reverse Transcription PCR

TE671 cells (0.5×10$^6$ to 1.0×10$^6$) were transfected using DOTAP (Boehringer Mannheim) with expression vectors encoding individual regulatory genes. Forty-eight hours later cells were lysed in situ using RNA$_{ZOl}$ B (Biotecx Laboratories, Inc.), and total cellular RNA was prepared according to standard methodology. cDNA was prepared by reverse transcription using random 6-mer primers and Moloney murine leukemia virus reverse transcriptase. An aliquot of cDNA was used as a template in PCR amplification. As a control for possible genomic DNA contamination, aliquots of RNA not subject to reverse transcription were used as templates in PCR.

Analysis of HIV-1 p24$^{gag}$ Antigen Production

For analysis of the infectivity of TE671 and TE671Ψ, cells were grown to 80% confluence in tissue culture flasks, then incubated with filtered (0.2 μm pore size) supernatants from HUT-78 cells chronically infected with HIV1 (strain RF). One day later cells were washed once with phosphate-buffered saline containing trypsin (2.5 mg./ml), then twice with culture medium to remove residual virus used to infect the cells. Supernatants were collected at 24 hr intervals with the first collection occurring immediately after the wash step. Detection of p24$^{gag}$ antigen was performed using an HIV1 p24 antigen assay kit (Coulter Immunology, Coulter Corporation) as per the manufacturer's instructions. This method employs an antigen-capture enzyme-linked immunosorbent assay. Wells were analyzed for absorbance at 450 nm on a Dynatech MR5000 enzyme-linked immunosorbent assay reader.

Transfections for Differentiation Studies

For differentiation experiments TE671 cells were transfected either by electroporation or with the lipid-mediated method using DOTAP. Though DOTAP produced more efficient transfections than electroporation, identical results were obtained with both methods with respect to differentiation. RD and D17 cells were transfected using DOTAP. Briefly, electroporation was performed with a Bio-Rad GenePulser and Pulse Controller on 2×10$^4$ to 5×10$^4$ cells harvested in log phase growth. DOTAP transfection was performed as per the manufacturer's instructions in tissue culture flasks on 0.5×10$^4$ to 1×10$^4$ in log phase growth. In either case selection medium was added 48–60 hr after transfection, and cells were maintained in selection for the duration of the experiments. Cells transfected with plasmids containing the puromycin resistance gene (puromycin acetyltransferase) were selected in 1 μg/ml puromycin. Neomycin selection was in mg/ml G418.

Anti-myosin Photomicrographic Immunofluorescence Assay

TE671 cells were transfected with the vpr expression vector, and 48 hr later the cells were trypsinized, transferred to glass slides, and selected with puromycin for 5 days prior to staining. Rapidly proliferating untransfected TE671 cells were grown on glass slides for 2–4 days before staining. Permeabilization and fixation were performed with 100% methanol at −20° C. for 10 min. The remaining steps were performed in PHEM buffer, which consists of 25 mM HEPES, 60 mM PIPES, 10 mM EGTA, and 2 mM MgCl$_2$ (pH 6.9). The fixed cells were washed three times with PHEM in between each step. Cells were first blocked with 5% normal goat serum to reduce nonspecific staining. Murine monoclonal antibody MY-32, which is specific for the myosin heavy chain of fast-twitch (type II) skeletal muscle (Sigma number M-4276), was then incubated with the specimens. As a negative control, an isotype-matched antibody (SIM.4 anti-CD4, obtained through the AIDS Research and Reference Reagent Program from Dr. James Hildreth) was used as primary antibody on some cells. Rhodamine-conjugated goat anti-mouse immunoglobulin G (TAGO) was used as secondary antibody, or alternatively a peroxidase-conjugated secondary antibody was used (Boehringer Mannheim). The cells were washed with PHEM, then examined under a fluorescence microscope and photographed.

Infection Assay

CD4+ TE671Ψ or CD4− TE671 cells were plated into tissue culture at very low confluence (<5%). One day later, supernatant and infected cells were added from HIV-1 (strains RF or MN)-infected CD4+ HUT-78 T lymphoma cells. The following day the infected cells were washed from the culture, and fresh medium was added to the cells. Cells were examined for differentiation beginning on the second day after infection.

Results

Differentiation of TE671 Following Transfection with Genomic Construct pNLpuro

A drug-selectable env deletion mutant HIV-1 genomic plasmid, pNLpuro, based on the HIV-1 infectious molecular clone pNL43 was construct. pNLpuro was transfected into the human rhabdomyosarcoma cell line TE671 and selected for stable transfectants. TE671 cells normally grow as small mononuclear round or polygonal fibroblast-like adherent cells about 3–7 μm in length and developed long, sometimes branched, processes. Some cells became large, flat, and irregularly shaped. Differentiating cells often became bi- or multinucleated, though cells with long processes that resembled myotubes lacked the linear arrangement of many nuclei that is found in true myotubes. The large cells remained fully viable for several weeks.

The differentiation of TE671 cells via chemical agents is a well-described phenomenon, as this cell line has been used as a model for skeletal muscle differentiation. Some agents, including protein kinase C-activating phorbol esters, as well as serum depleted medium, will induce TE671 cells to undergo alterations in both morphology and growth characteristics that parallel in many aspects the differentiation of myoblasts into myotubes. Phorbol myristate acetate-stimulated TE671 cells increase in overall size and length, are often multinucleated, and display slowed proliferation. On the other hand, no morphologically differentiated pNLpuro-transfected cells were observed to divide when followed for up to 10 days.

Determination of HIV-1 Elements Sufficient to Differentiation

To define the viral gene(s) responsible for induction of cell differentiation in the rhabdomyosarcoma cell line, individual HIV-1 regulatory genes were examined, as some of their protein products have been reported to influence cellular events. A tat expression vector (Arya, S. K., et al., (1985) *Science* 229:69–73) was obtained and modified to permit selection of stably transfected cells. The env-rev region of HIV-1 was amplified by the polymerase chain reaction (PCR) from an HIV-1 molecular clone and subcloned directly into the pCDNAl/neo expression vector. To clone the remaining regulatory genes into expression vectors, the single open reading frame of each gene was amplified using PCR. During the PCR amplification a consensus ribosome initiation sequence was introduced immediately upstream of each start codon. The genes encoding the regulatory proteins nef, vpr, vif, and vpu were amplified by this method and subcloned into the pBABE-puro expression vector.

Each plasmid was transfected into TE671 cells and selected on the appropriate antibiotic. Expression of rev was demonstrated indirectly by showing expression of envelope protein (env) in Western blot and cell fusion assays. Since expression of env is dependent on a critical threshold level of rev expression, it can be deduced that physiologically relevant levels of rev were produced. The vpr protein expressed from the vpr vector showed a single 15 kd species by Western blot analysis. Cellular expression of tat, vif, vpr, vpu, and nef was demonstrated by reverse transcription PCR analysis. PCR products were run on 2% agarose gels and stained with ethidium bromide for photography. As a control against possible DNA carryover in the RNA preparations, RNA that was not subjected to reverse transcription was used as template in PCR.

Expression of vpu, vif, tat, nef, rev and env failed to induce significant morphological changes in TE671 cells. Vpr expression, on the other hand, induced profound differentiation in the majority of transfected cells.

To verify that TE671 differentiation involves the development of the well-defined muscle phenotype and not a novel program, vpr-transfected TE671 cells were stained with an antibody specific for the heavy chain of fast-twitch skeletal-muscle myosin, which is expressed at high levels only in mature skeletal muscle cells. Antibody MY-32 reacted strongly with vpr-transfected TE671 cells. The majority of untransfected TE671 cells expressed low levels of myosin, though, as previously reported for TE671, a few untransfected cells stained weakly for myosin. Staining with an isotype-matched control antibody was negative for both transfected and untransfected TE671 cells.

The transfection efficiency achieved by the vpr vector was equal to the efficiency of transfection of the other vectors. Transfection efficiency was determined by the number of cells remaining after selection in puromycin for 2 days, which is sufficient time to kill all nontransfected cells. After several more days, there appeared to be many fewer cells in the vpr culture than in the non-vpr cultures, owing to the continued replication of the cells in the non-vpr cultures. Not all cells transfected with either the genomic pNLpuro plasmid or with vpr alone underwent morphological differentiation, however. This result is consistent with the heterogeneous response observed in rhabdomyosarcoma lines subjected to differentiation-inducing conditions. More cells remained undifferentiated in the vpr-transfected cultures (10%–20%) than in the pNLpuro cultures (<1%). The equal transfection efficiency in the vpr culture indicates that vpr did not kill replicating cells and leave alive only the naturally occurring spontaneously differentiated cells, which could in theory produce a false interpretation that vpr can induce differentiation. The absolute number of differentiated cells in the HIV vpr-transfected cultures was always higher than that found in the other regulatory gene transfections or in untransfected TE671 cells, further indicating that vpr induced differentiation, rather than "revealing" otherwise differentiated cells. Additionally, cells of the radical phenotype observed in the HIV vpr transfected cultures were never observed in the untransfected controls or in the cells transfected with other regulatory genes.

Other Cells are Affected by vpr

The vpr gene was transfected into the TE671-related rhabdomyosarcoma line RD and the osteogenic sarcoma (osteosarcoma) line D17 to examine the generality of the effects observed in TE671. Following drug selection of the transfected cells, a radical alteration in size and morphology was observed in both cell lines. Inhibition of proliferation was observed in both lines. Time-lapse video microscopy of D17 cells showed them to be very active. The central or perinuclear regions of many cells rotated with a period of approximately 2 hr, frequently resulting in a distinct crescent shape. The majority of the large cells in both cultures remained viable for at least 2 weeks and did not proliferate, though some small proliferating cells remained in both the D17 and RD transfectants, as was observed in the TE671 cultures. The D17 osteosarcoma cells did not express increased levels of alkaline phosphatase, however, which is a marker for bone maturation.

Deletion of vpr from the HIV-1 Genome

Whether vpr is necessary for HIV-1-induced differentiation was next examined. To this end, a vpr deletion mutant of the HIV⁻ env plasmid pNLpuro called pNLpuroΔvpr was constructed. A stop codon was introduced after amino acid 22 of vpr, and 122 nt were removed from the coding region of vpr from amino acid 22 to amino acid 62. First, whether deletion of the vpr gene affected the expression of HIV-1 genes was tested since such an effect might complicate the interpretation of experiments. Viral protein expression following transfection with pNLpuroΔvpr was equal to expression from pNLpuro, as measured by $p24^{gag}$ protein released into the culture medium. Since expression of structural genes by HIV is dependent on successful expression of both tat and rev proteins, it is apparent that the mutation introduced into the genome did not result in a general disturbance of HIV transcription or RNA splicing. As a further control to examine the effect of deletion of vpr on HIV-1 expression, a vpr deletion mutant was constructed from wild-type pNL43, by the same method as that used for the vpr deletion mutant of pNLpuro, to yield the env construct, pNLΔvpr. When transfected into TE671Ψ CD4⁺ transfectant of TE671, syncytia were efficiently produced by both the vpr and vpr⁺ constructs. Despite nearly equivalent HIV-1 protein production between pNLpuro and pNLpuroΔvpr, the outcome of transfection with the vpr deletion mutant, with respect to differentiation, was clearly different from that of transfection with the vpr⁺ HIV1 genome. While cells transfected with pNLpuro differentiated, the majority of the TE671 cells transfected with the vpr deletion mutant pNLpuroΔvpr showed either no change or a small and transient increase in size and length. Though a few myosin-staining morphologically differentiated cells were produced in each transfection, the efficiency of this effect varied from experiment to experiment and was never seen to exceed 10% of the cells remaining after drug selection. Taken together these results (summarized in Table 1) demonstrate that HIV-1-induced differentiation of TE671 cells is a function primarily of the vpr gene.

$p24^{gag}$ production in pNLpuroΔvpr continued for 2–3 weeks following transfection and subculture, whereas p24 released from pNLpuro-transfected cells was eliminated following subculture. Subculture effectively eliminated the large differentiated cells, leaving only the replicating undifferentiated cells intact. Therefore, only the differentiated cells released virus in the pNLpuro-transfection experiments. Exposure of the transfectants to the protein kinase C-activating phorbol ester phorbol myristate acetate, which has been shown to stimulate HIV-1 expression in chronically infected cells (Harada, S., et al., (1986) *Virology* 154:249–258), resulted in a 3-fold increase in p24 release from the pNLpuroΔvpr-transfected cells but no measurable p24 release from the undifferentiated pNLpuro-transfected cells. This result indicates that, in the presence of vpr, HIV-1 production in TE671 cells is incompatible with their replication, whereas in the absence of vpr, HIV1 expression can continue in replicating cells. These cells retain the ability to differentiate in response to various agents and thus remain relatively unaffected by HIV-1 expression.

Demonstration that Infection with HIV-1 Induces Differentiation

The ability of HIV infection to induce differentiation of the rhabdomyosarcoma cell line was examined. For these experiments, the cell line TE671Ψ was used. TE671Ψ expresses high levels of CD4 on its cell surface and can be infected with HIV at very high efficiency, resulting in a high level of viral production. Infection of TE671Ψ cells at or near confluence results in cell fusion into giant multinucleated syncytia, owing to the fusion of cell membranes following coexpression of HIV envelope proteins and their receptor, CD4. To allow infection and maintenance in culture of unfused cells for several days following infection, TE671Ψ was plated at low cell density, typically 5% confluence or less. Cells plated at low cell density and left unexposed to HIV-1 did not differentiate and continued to replicate. Cells infected with HIV-1 (strains RF or MN) differentiated in a manner very similar to that observed following transfection with the pNLpuro viral genome. These results demonstrate that HIV infection can directly induce cell differentiation.

Discussion

The unexpected observation that transfection of HIV-1 genomic DNA into the embryonal rhabdomyosarcoma line TE671 induced cell growth inhibition and differentiation is reported here. Infection of TE671 via a transfected CD4 molecule resulted in the same outcome, indicating that the effects did not result from transfection artifacts and have relevance to natural HIV infection. Transfection and expression of each regulatory gene of HIV-1 in the cell line revealed that the vpr gene can produce the growth inhibition and morphological differentiation that the whole virus induces. Activation of the endogenous muscle program was demonstrated by showing that the vpr-transfected cells expressed high levels of fast-twitch myosin, while the majority of untransfected cells did not. Transfection of a vpr deletion mutant into TE671 cells resulted in the production of large numbers of replicating undifferentiated cells that continued to produce high levels of viral protein. These results indicate that vpr is the primary determinant for differentiation and growth inhibition in TE671 cells. Transfection of vpr into the rhabdomyosarcoma line RD and the osteosarcoma line D17 resulted in cessation of proliferation, gross morphological changes, and profound enlargement. Thus vpr may be a regulator of cell function in cells of diverse origin.

Muscle differentiation has been well studied in rhabdomyosarcomas and in normal cells. Expression of helix-loop-helix transcription factors such as MyoD in normal myoblasts leads to differentiation into mature postmitotic myotubes. In most embryonal rhabdomyosarcomas, despite expression of MyoD, withdrawal from the cell cycle and differentiation are inhibited. Transformation of embryonal rhabdomyosarcomas is linked to expression of an activated ras oncogene, loss of a putative tumor suppressor on chromosome 11, and constitutive expression of autocrine fibroblast growth factor and transforming growth factor β. In addition, RD (and therefore TE671) has been shown to lack a wild-type p53 tumor suppressor gene. p53 expression has recently been associated with cell cycle control and the regulation of DNA repair mechanisms, cellular events linked to retroviral integration. Osteosarcomas exhibit features of bone matrix-secreting osteoblasts but are thought to arise from multipotential mesenchymal tissue and therefore to represent similarly a disregulation of primitive cells. These tumors also typically display loss-of-function p53 mutations. Vpr can at least partially overcome the block on differentiation and completely restore inhibition of cell proliferation; therefore, vpr may either replace a function lost during transformation or activate a pathway that overrides the genetic defects.

These studies directly demonstrate that the HIV-1 vpr gene encodes a protein that can function in the regulation of basic cellular events. The outcome of this regulation is observed here as an inhibition of cell proliferation and the induction of differentiation.

Example 2

A pharmaceutical composition is formulated by providing 100 μg/μl pBabe-puro+vpr combined with sterile phosphate buffered saline that is isotonic with cells. The composition is administered by direct injection into a solid tumor mass of an individual.

Example 3

DNA encoding HIV-1 vpr protein is amplified via PCR from the HIV-1 genomic plasmid pNL43 using the PCR primers and strategy described in Example 1. The resulting PCR product is inserted into expression vector plasmid pSE420 (Invitrogen, San Diego, Calif.) and introduced into E. coli.

A pharmaceutical composition is prepared by isolating vpr protein form the cells and/or medium and combining it with a sterile pharmaceutically acceptable solution.

Example 4

DNA encoding HIV-1 vpr protein is amplified via PCR from the HIV-1 genomic plasmid pNL43 using the PCR primers and strategy described in Example 1. The resulting PCR product is inserted into expression vector plasmid pYES2 (Invitrogen, San Diego, Calif.) and introduced into S. cerevisiae.

A pharmaceutical composition is prepared by isolating vpr protein form the cells and/or medium and combining it with a sterile pharmaceutically acceptable solution.

Example 5

DNA encoding HIV-1 vpr protein is amplified via PCR from the HIV-1 genomic plasmid pNL43 using the PCR primers and strategy described in Example 1. The resulting PCR product is inserted into expression vector plasmid pcDNA I (Invitrogen, San Diego, Calif.) and introduced into Chinese Hamster Ovary (CHO) cells.

A pharmaceutical composition is prepared by isolating vpr protein form the cells and/or medium and combining it with a sterile pharmaceutically acceptable solution.

Example 6

Recombinant vpr protein was produced in baculovirus. Production of recombinant vpr protein allowed for studies of the function of the protein in vitro, permitted the generation of anti-vpr antibodies in rabbits and monoclonal antibodies in mice.

The vpr gene was cut out of the vpr-pBabe-puro construct. This insert was then introduced into the baculovirus expression vector pVL-1393 (PharMingen) by standard techniques. Recombinant viruses were produced as previously described (Matsuura et al. 1987) using Baculogold (PharMingen) linearized DNA in cotransfection experiments into Spodoptera fungupeida (SF-9) cells. SF-9 cells and the subsequent viral infections were carried out as previously described (Matsuura et al. 1987, O'Reilly et al. 1991). The presence of recombinant virus was easily observed under the light microscope following transfection. The presence of vpr protein was tested by Enzyme linked immuno-sorbent assay (ELISA) and western Blot analysis, using a rabbit anti-peptide (amino acids 2–21 N-terminus) polyclonal serum obtained through the AIDS repository.

Sf-9 cells were infected with recombinant virus at a multiplicity of infection of 5–10 and harvested at various times post infection. Whole cell and supernatant fractions were analyzed by ELISA using the aforementioned antibody. As early as 24 hours post infection, recombinant protein could be found in the supernatant. This presence would reach its peak at 30 hrs. post infection. Fractionation experiments were undertaken to optimize the collection of vpr protein. The majority of the vpr reactivity was found to be located in supernatant of recombinant Sf-9 cells. Little additional vpr protein was recovered from nonionic detergent lysates of cell sonicates.

The activity of this protein was further verified by screening the protein containing cell culture supernatant with a mixture of HIV+ seropositive patient samples as well as control samples. HIV patients have been reported to produce an humoral immune response to the vpr gene product. Immulon II ELISA plates (Dynatech laboratories, Chantilly, Va.) were coated with three dilutions of the vpr supernatant. These were then probed with 2 serial dilutions of heat inactivated patient sera. Our results demonstrate that HIV positive patient sera did react with the vpr present in the cell supernatant. The level of their reactivity was not correlated to the levels of reactivity the sera contained against the HIV-1 envelope (as measure by solid phase ELISA).

Rabbit anti-vpr protein was titrated to 1/1000 dilution and used in ELISA assay to determine production of vpr by various Sf-9 cell preparations. Specific and significant reactivity was observed in supernatant fraction from vpr transfected cells only. The rabbit antisera is an epitope restricted anti-peptide antisera and as such may not recognize a poorly processed insoluble cell associated vpr fraction in these cells. To confirm vpr production the identical samples were reacted with pooled HIV patient sera and pooled normal human sera was used as a specific control. HIV positive patient sera reacted with the supernatant containing fraction in a similar manner to the rabbit antisera. These same sera samples reacted very poorly with supernatants from non-infected Sf-9 cells. The same patient sera reacted poorly with supernatants from Sf-9 cells which were infected with control recombinant viruses (viruses which were formed by cotransfecting linearized DNA and pVL 1393 alone). The reactivity observed demonstrates the production of vpr protein in the supernatants of Sf-9 infected cells.

The vpr protein containing supernatant was subjected to purification by two different chromatography methods.

Supernatants from infected Sf-9 cells were concentrated in an amicon pressure filter unit, dialyzed, clarified and treated with protease inhibitors prior to column chromatography. The 24 hour vpr product in the supernatant was concentrated, centrifuged at 10000 g for 10 min. Protease inhibitor were then added to this supernatant (PMSF, aprotonin, leupeptin and EDA) at their appropriate concentrations. This solution was then passed over a protein A-rabbit anti-vpr column. Rabbit anti-vpr immunoglobulin was purified on a protein A-agarose column and eluted and dialyzed and then coupled to CNBr-sepharose 4B beads according to the manufacturers instructions (Sigma). This column was then utilized for immunoaffinity chromatography of baculovirus vpr. Vpr was eluted in a pH gradient. The column was then washed with PBS. 10 mM Na-Phosphate, ph 8.0, and elution by a pH gradient was undertaken. Specific reactivity appeared to be concentrated over a limited fraction number as determined by rabbit anti-vpr antisera reactivity in ELISA. The specific protein peak and activity peak clearly overlap.

In addition, vpr protein was collected off a DEAE sepharose column using a salt gradient. Baculovirus-vpr protein containing supernatant was treated as above and then placed over a DEAE-sepharose column. The column was eluted by salt gradient, vpr activity was concentrated over a limited range.

Both purification procedures generate samples which react with HIV patient samples as well as the rabbit anti-vpr peptide antisera in ELISA and in western blotting experiments. In western blotting experiments, a 26Kd protein is present a dominant 14Kd protein and two small protein bands suggestive of breakdown products are observed. The 26Kd band may represent an artifact of purification (such as acetylation) or may indicate a state of aggregation requiring further investigation.

Example 7

DNA encoding HIV-1 vpr protein was amplified via PCR from the HIV-1 genomic plasmid pNL43 using the PCR primers and strategy described in Example 1. The resulting PCR product is inserted into expression vector plasmid of the MaxBacm™ (Invitrogen, San Diego, Calif.) complete baculovirus expression system and introduced into insect cells used in that system.

A pharmaceutical composition is prepared by isolating vpr protein form the cells and/or medium and combining it with a sterile pharmaceutically acceptable solution.

Example 8

Glioblastoma cell lines were tranfected with the vpr expression vector and specific examples of differentiation events were observed. For differentiation experiments the cells were transfected either by a lipid-mediated method using DOTAP (Boehringer Mannheim). DOTAP (Boehringer Mannheim) transfection was performed per the manufacturer's instructions in tissue culture flasks on 0.5–1×10$^6$ cells in log phase growth. Selection medium was added 48–60 hours post transfection and cells were maintained in selection for the duration of the experiments. Cells transfected with plasmids containing the puromycin resistance gene (PAC) were selected in 1 µg/ml puromycin (Sigma) For both the cell lines U87-MG and U138 MG specific morphological differentiation was observed. In comparison to control transfected cells the vpr transfected cells exhibited extended pseudopods and demonstrated neurite outgrowth concurrent with an observed inhibition of their cellular proliferation. Both cell lines also demonstrated an increased cytoplasmic to nuclear ratio as well as a clear enlargement in cell size. Frequent bipolarity was also observed in the vpr transfected cell lines along with active cytoskeletal activity.

Test assays comprise the steps of adding test compound to the to the medium used in the cell cultures. Test compound is provided in 10 dilutions ranging from 10 µM to 100 µM.

A control assay may optionally be run comprising the step of adding vpr protein to cells without adding test compound.

Analysis of non-specific and lineage specific markers in these cell lines is performed 2 to 14 days post transfection.

Example 9

A screen for identifying compounds which inhibit vpr's ability to induce differentiation of undifferentiated cells is performed as follows.

Either the human embryonal rhabdomyosarcoma TE671 line (ATCC HTB 139) and the canine osteosarcoma D17 line (ATCC CLL 183) are used. The cells are maintained in appropriate cell culture medium under standard conditions. Vpr is produced as described in Examples 3, 4, 5 or 6.

Test assays comprise the steps of contacting the cells with vpr in the presence of a test compound. A mixture of vpr and the test compound are added to the cell culture medium together or separately. Test compound is provided in 10 dilutions ranging from 10 µM to 100 µM.

A control assay may optionally be run comprising the step of adding vpr protein to cells without adding test compound.

After 2–14 days, cells are observed to determine whether differentiation has occurred. Morphological and size changes indicating differentiation are described in Example 1. Visual observation may be accompanied by or substituted with an antibody assay to observed whether myosin is being produced by the cells. Anti-myosin assay is performed as described in Example 1.

Example 10

A simple in vitro ELISA based system for mapping interaction sites between vpr and gag p55. Baculovirus produced vpr as outlined above and baculovirus gag produced by similar means were used in binding assays. ELISA plates were coated with gag or vpr and reacted with specific antisera as controls, or coated with dilutions of gag protein followed by vpr and sandwiched with anti-vpr antibodies. Alternatively, plates were coated with dilutions of vpr followed by gag protein and sandwiched with anti-gag specific antisera. Controls for specificity include that gag antisera does not react with vpr, vpr antisera does not react with gag, neither gag nor vpr antisera reacts with BSA. Plates were coated with recombinant antigen in carbonate buffer, washed extensively, blocked with PBS/1% BSA and then washed extensively, secondary protein was dissolved in PBS/BSA and incubated at 4C 1 hr, then washed extensively and reacted with specific antisera. Specific sandwich activity was detected in both directions as described above.

Example 11

Using PCR and recombinant DNA technology, truncation mutants of the vpr gene were constructed and cloned into pBABE expression plasmids. These constructs delete vpr in approximately 20AA groups from the carboxy terminus traveling in toward the amino terminus of the protein. The resulting protein products are 72AA, 50AA and 30AA.

Preliminary studies indicate that the carboxyl terminus 24AA of vpr is necessary for induction of differentiation of both the rhabdomyosarcoma and glial cell lineages as loss of the inhibition of proliferation and loss of morphological changes with the deletion mutants has been observed. One interesting observation of these studies is that this carboxy region contains a significant region of homology with the muscle oncogene ski. The avian retroviral oncogene ski shows properties resembling those described for vpr (Colmenares and Stavnezer, *Cell*, 1989).

Studies suggest that carboxy terminal deletion vpr mutants still retain gag binding activity in this system. This assay therefore differentiates the functional region of vpr which interacts with gag and the functional region for cell differentiation function.

Example 12

Antibodies and Immunizations

Rabbit anti-vpr peptide serum (Garrett, et al., *J. Virol.*, 1991, 65, 1653) (a.a. 2–21: Cys-Glu-Gln-Ala-Pro-Glu-Asp-Gln-Gly-Pro-Gln-Arg-Glu-Pro-His-Asn-Glu-Trp-Thr-Leu- Glu; SEQ ID NO:4) was obtained from Dr. Brian Cullen through the NIH AIDS Research and Reference Reagent Program. To produce additional rabbit antibodies against vpr, a rabbit was immunized with 10–20 µg of partially purified vpr protein (produced as described below from the anti-vpr column) in complete Freund's adjuvant (CFA) once, then with incomplete adjuvant (IFA) for subsequent immunizations. Final immunization was with 50 µg of each of three keyhole limpet hemocyanin (KLH)-coupled vpr peptides in IFA. Peptides were purchased from American Bio-Technologies. Sequences of peptides: vpr 9–20 (Gly-Pro-Gln-Arg-Glu-Pro-His-Asn-Glu-Trp-Thr-Leu; SEQ ID NO: 5), 41–55 (Gly-Leu-Gly-Gln-His-Ile-Tyr-Glu-Thr-Gly-Asp-Thr-Trp-Ala; SEQ ID NO: 6), 81–96 (Ile-Gly-Val-Thr-Gln-Gln-Arg-Arg-Gln-Arg-Asp-Gly-Ala-Ser-Arg-Ser; SEQ ID NO:7). To produce mouse anti-vpr serum, Balb-c mice were immunized with 20 µg of single peptides coupled to KLH in CFA for the first immunization and IFA for subsequent immunizations.

Example 13

Column Chromatography

Affinity columns were constructed according to Harlow and Lane. Harlow, E. and Lane, E., *Antibodies: A Laboratory Manual*, 1988, Cold Spring Harbor Laboratory Press which is incorporated herein by reference. The IgG fraction of 250 µl of the rabbit peptide serum was bound to 1 ml of protein A agarose beads (Gibco BRL), washed in 0.2 M sodium borate buffer (pH 9.0) and coupled with 20 mM dimethylpimelimidate (DMP). The polyclonal rabbit anti-vpr column was constructed according to the same procedure using 6 ml of serum and 3 ml of protein G agarose beads (Gibco BRL).

Example 14

Detection of Anti-vpr Antibodies by Capture ELISA

For detection of anti-vpr antibodies, an ELISA was performed using eukaryotically-produced vpr attached to solid phase, followed by the addition of the test sample. Peroxidase-coupled anti-human antibody was used for detection (Boehringer Mannheim). Color development was with 3,3',5,5'-tetramethylbenzidine dihydrochloride (TMB) (Sigma) according to the manufacturer's instructions. Anti-p24 antibodies were detected using recombinant p24 (American BioTechnologies) attached to solid phase support. Both recombinant proteins were used at an approximate concentration of 1 µg/ml, 50 µul/well. Incubation was done for 1 hour at 37° or 12 hours at 4°. Detection antibodies were used at a 1:15000 dilution as per manufacturers directions.

Example 15

Detection of vpr by Capture ELISA

For detection of vpr, a capture ELISA was performed. Rabbit anti-vpr peptide serum (reactive to aa 2–21) was immobilized in wells of a 96-well ELISA plate (Immulon II, Dynatech) in carbonate-bicarbonate buffer (0.2 M, pH 9.2). Detection of bound antigen was performed using a mouse anti-vpr peptide serum (reactive to aa 81–96) followed by peroxidase coupled anti-mouse antibody (Boehringer Mannheim). Color development was with TMB as described previously. The rabbit antibody was used at 1:1000, the mouse antibody was used at 1:800. Incubation was done for 1 hour at 37° or 12 hours at 4°. Anti-mouse antibodies were used at a 1:12000 dilution as per manufacturers directions.

Example 16

HIV Infection in Presence of vpr $10^5$ cells were suspended in media and infected with 25 $TCID_{50}$ of either Ba-L of NL43 HIV in the presence of either vpr or control supernatants. The cells were washed 12 hours post-infection to remove residual virus and vpr and then cultured under standard conditions of 5% $CO_2$ and 37° C. Retroviral growth was measured by a capture ELISA in which p24 was detected. This assay may be performed in the presence of serial dilutions of potential growth inhibitors to screen for such effects.

Some inhibitors of the vpr effect on viral infectivity include rabbit anti-vpr peptide (amino acids 2–12) #808 and rabbit anti-vpr that was made in baculovirus. Antisera was used at different dilutions: 1:20, 1:50, 1:250; 1:1000; 1:5000.

Example 17

Quantitative Virus Load Assay

Blood was obtained from an individual suspected of being $HIV^+$ and the cells were removed by centrifugation. To the individual's blood cells were added uninfected human target cells. Alternatively, the blood cells may be infected in vitro with other retroviruses and added to uninfected target cells. The mixture of infected cells and uninfected target cells was incubated in the presence or absence of vpr. The mixture was subsequently titrated for virus growth as described previously. This assay may be performed in the presence of serial dilutions of potential growth inhibitors to screen for such effects.

Example 18

Induction of p24-p6 Interaction

To determine whether a particular composition may modulate p24-p6 interaction, the following method may be employed. A 96-well microtiter plate is coated with an antibody composition, V7.8, reactive with p24 in a volume of buffer. The microtiter plate is incubated for a time sufficient for binding to occur and is subsequently washed with PBS to remove unbound antibody. The microtiter plate is blocked with a PBS/BSA solution to prevent nonspecific binding. Recombinant p24, obtained from American Bio-Technologies and used at 1.0 µg/ml, is added to the wells. Recombinant p6 is added to the wells. Serial dilutions of the particular composition or buffer are subsequently added to the wells and the microtiter plate is incubated for a time sufficient for binding to occur. Anti-p6 antibodies are added to the wells. The microtiter plate is incubated for a time sufficient for binding to occur and is subsequently washed with PBS to remove unbound labeled antibody. The amount of labeled and bound anti-p6 antibody is determined.

V7.8 is a human anti-p24 antibody used at 1:2000. The anti-p6 antibody was 1584 at 1:500. Incubation was done for 1 hour at 37° or 12 hours at 4°. Goat anti-rabbit HRP (Boehringer Mannheim) was used to identify anti-p6 antibody as per manufacturers directions.

Example 19

Induction of p24-p6 Interaction by Mab 1238

It has been discovered that an antibody, Mab 1238, enhances the interaction between p24 and p6 as well between p24 and vpr. Mab 1238 induces the aggregation of p24 in vitro. It has also been found that p15, but not p7, also induces the aggregation of p24 in vitro. Because p15 is cleaved into p7 and p6, and p15 but not p7 induces the aggregation of p24, it is thought that p6 may play a major role in p24 aggregation. Thus, p15- or Mab 1238-induced p24 aggregation may be utilized to screen for particular compounds which may disrupt p24 aggregation and subsequent HIV particle assembly. In addition, Mab 1238-enhanced p24-p6 or p24-vpr interaction may also be utilized to screen for particular compositions which may disrupt HIV particle assembly. Therefore, this procedure would be an extremely significant assay for screening potential therapeutic compounds for HIV therapy.

Mab 1238-enhanced p24-p6 or p24-vpr interaction may also be utilized to screen for particular compositions which may disrupt HIV particle assembly. Therefore, this procedure would be an extremely significant assay for screening potential therapeutic compounds for HIV therapy.

A 96-well microtiter plate was coated with an antibody composition, V7.8, reactive with p24 in a volume of buffer. The microtiter plate was incubated for a time sufficient for binding to occur and was subsequently washed with PBS to remove unbound antibody. The microtiter plate was then blocked with a PBS/BSA solution to prevent nonspecific binding. Recombinant p24, obtained from American Bio-Technologies and used at 1.0 µg/ml, was added to the wells. Recombinant p6 was added to the wells. Mab 1238, used at a dilution of 1:10 from the stocks provided by the NIH AIDS Repository, was added to the wells and the microtiter plate was incubated for a time sufficient for binding to occur. Anti-p6 antibodies were added to the wells. The microtiter plate was incubated for a time sufficient for binding to occur and was subsequently washed with PBS to remove unbound labeled antibody. The amount of labeled and bound anti-p6 antibody was determined as described above. All quantities, unless otherwise noted, were the same as those used above.

Example 20

Inhibition of p24-p6 Interaction

To determine whether a particular composition may inhibit p24-p6 interaction, the following method may be employed. A 96-well microtiter plate is coated with an antibody composition, V7.8, reactive with p24 in a volume of buffer. The microtiter plate is incubated for a time sufficient for binding to occur and is subsequently washed with PBS to remove unbound antibody. The microtiter plate is blocked with a PBS/BSA solution to prevent nonspecific binding. Recombinant p24, obtained from American Bio-Technologies and used at 1.0 µg/ml, is added to the wells. Recombinant p6 is added to the wells. Mab 1238, used at a dilution of 1:10 from the stocks provided by the NIH AIDS Repository, is added to the wells. Serial dilutions of the particular composition or buffer are subsequently added to the wells and the microtiter plate is incubated for a time sufficient for binding to occur. Anti-p6 antibodies are added to the wells. The microtiter plate is incubated for a time sufficient for binding to occur and is subsequently washed with PBS to remove unbound labeled antibody. The amount of labeled and bound anti-p6 antibody is determined as described above. All quantities, unless otherwise noted, are the same as those used in above.

Example 21

Induction of p24-vpr Interaction

To determine whether a particular composition may modulate p24-vpr interaction, the following method may be employed. A 96-well microtiter plate is coated with an antibody composition, V7.8, reactive with p24 in a volume of buffer. The microtiter plate is incubated for a time sufficient for binding to occur and is subsequently washed with PBS to remove unbound antibody. The microtiter plate is blocked with a PBS/BSA solution to prevent nonspecific binding. Recombinant p24 is added to the wells. Eukaryotically-produced vpr is added to the wells. Serial dilutions of the particular composition or buffer are subsequently added to the wells and the microtiter plate is incubated for a time sufficient for binding to occur. Anti-vpr antibodies, obtained as described previously, are added to the wells. The microtiter plate is incubated for a time sufficient for binding to occur and is subsequently washed with PBS to remove unbound labeled antibody. The amount of labeled and bound anti-vpr antibody is determined. All quantities, unless otherwise noted, are the same as those used above.

The recombinant p24 are added to the wells at 1 µg/ml. The anti-vpr antibodies are used at 1:1000 and followed by labelled secondary antibodies (either anti-rabbit HRP or anti-mouse HRP).

Example 22

Induction of p24-vpr Interaction by Mab 1238

A 96-well microtiter plate was coated with an antibody composition, V7.8, reactive with p24 in a volume of buffer. The microtiter plate was incubated for a time sufficient for binding to occur and was subsequently washed with PBS to remove unbound antibody. The microtiter plate was then blocked with a PBS/BSA solution to prevent nonspecific binding. Recombinant p24 was added to the wells. Eukaryotically-produced vpr was also added to the wells. Mab 1238, used at a dilution of 1:10 from the stocks provided by the NIH AIDS Repository was added to the wells. Anti-vpr antibodies, obtained as described previously, were added to the wells. The microtiter plate was incubated for a time sufficient for binding to occur and was subsequently washed with PBS to remove unbound labeled antibody. The amount of labeled and bound anti-vpr antibody was determined as described above. All quantities, unless otherwise noted, were the same as those used above.

Example 23

Inhibition of p24-vpr Interaction

To determine whether a particular composition may enhance p24-vpr interaction, the following method may be employed. A 96-well microtiter plate is coated with an antibody composition, V7.8, reactive with p24 in a volume of buffer. The microtiter plate is incubated for a time sufficient for binding to occur and is subsequently washed with PBS to remove unbound antibody. The microtiter plate is blocked with a PBS/BSA solution to prevent nonspecific binding. Recombinant p24 is added to the wells. Eukaryotically-produced vpr is also added to the wells. Mab 1238, used at a dilution of 1:10 from the stocks provided by the NIH AIDS Repository, is added to the wells. Serial dilutions of the particular composition or buffer are subsequently added to the wells and the microtiter plate is incubated for a time sufficient for binding to occur. Anti-vpr antibodies, obtained as described previously, are added to the wells. The microtiter plate is incubated for a time sufficient for binding to occur and is subsequently washed with PBS to remove unbound labeled antibody. The amount of labeled and bound anti-vpr antibody is determined as described above. All quantities, unless otherwise noted, are the same as those used above.

Example 24

Modulation of p24 Aggregation

To determine whether a particular composition may enhance p24 aggregation, the following method may be employed. A 96-well microtiter plate is coated with an antibody composition, V7.8, reactive with p24 in a volume of buffer. The microtiter plate is incubated for a time sufficient for binding to occur and is subsequently washed with PBS to remove unbound antibody. The microtiter plate is blocked with a PBS/BSA solution to prevent nonspecific binding. Recombinant p24 is added to the wells. Serial dilutions of the particular composition or buffer are subsequently added to the wells and the microtiter plate is incubated for a time sufficient for binding to occur. Sheep anti-p24 antibodies, obtained from the NIH Repository and used at a dilution of 1:600 from the stock provided, are added to the wells. The microtiter plate is incubated for a time sufficient for binding to occur and is subsequently washed with PBS to remove unbound labeled antibody. A secondary peroxidase-conjugated, goat anti-sheep antibody (Boehringer Mannheim) is added to the wells at 1:12000. The amount of labeled and bound anti-p24 antibody is determined by peroxidase color development as known to those skilled in the art. All quantities, unless otherwise noted, are the same as those used above.

Example 25

Enhancement of p24 Aggregation by Mab 1238 or p15

A 96-well microtiter plate was coated with an antibody composition, V7.8, reactive with p24 in a volume of buffer. The microtiter plate was incubated for a time sufficient for binding to occur and was subsequently washed with PBS to remove unbound antibody. The microtiter plate was blocked with a PBS/BSA solution to prevent nonspecific binding. Recombinant p24 was added to the wells. Mab 1238, used at a dilution of 1:10 from the stocks provided by the NIH AIDS Repository, was added to the wells. Alternatively, p15 was added to the wells. Anti-p24 antibodies were added to the wells. The microtiter plate was incubated for a time sufficient for binding to occur and was subsequently washed with PBS to remove unbound labeled antibody. The amount of labeled and bound anti-p24 antibody was determined as described above. All quantities, unless otherwise noted, are the same as those used above.

Example 26

Inhibition of p24 Aggregation

To determine whether a particular composition may inhibit p24 aggregation, the following method may be employed. A 96-well microtiter plate is coated with an antibody composition, V7.8, reactive with p24 in a volume of buffer. The microtiter plate is incubated for a time sufficient for binding to occur and is subsequently washed with PBS to remove unbound antibody. The microtiter plate is blocked with a PBS/BSA solution to prevent nonspecific binding. Recombinant p24 is added to the wells. Mab 1238, used at a dilution of 1:10 from the stocks provided by the NIH AIDS Repository, is added to the wells. Serial dilutions of the particular composition or buffer are subsequently added to the wells and the microtiter plate is incubated for a time sufficient for binding to occur. Anti-p24 antibodies are added to the wells. The microtiter plate is incubated for a time sufficient for binding to occur and is subsequently washed with PBS to remove unbound labeled antibody. The amount of labeled and bound anti-p24 antibody is determined as described above and all quantities, unless otherwise noted, are the same as those described above.

Example 27

Inhibition of p24 Aggregation by α-helical Peptide

A 96-well microtiter plate was coated with an antibody composition, V7.8, reactive with p24 in a volume of buffer. The microtiter plate was incubated for a time sufficient for binding to occur and was subsequently washed with PBS to remove unbound antibody. The microtiter plate was blocked with a PBS/BSA solution to prevent nonspecific binding. Recombinant p24 was added to the wells. Mab 1238, used at a dilution of 1:10 from the stocks provided by the NIH AIDS Repository, was added to the wells. Serial dilutions of the α-helical peptide or buffer were subsequently added to the wells and the microtiter plate was incubated for a time sufficient for binding to occur. Anti-p24 antibodies were added to the wells. The microtiter plate was incubated for a time sufficient for binding to occur and was subsequently washed with PBS to remove unbound labeled antibody. The amount of labeled and bound anti-p24 antibody was determined as described above. All quantities, unless otherwise noted, were the same as those used above.

Example 28

Production of Eukaryotic vpr

To construct a recombinant baculovirus containing the vpr gene, the vpr open reading frame and a PCR-introduced consensus eukaryotic ribosome binding sequence, from the vpr-pBabe-puro expression plasmid previously described (Levy et al., *Cell*, 1993, 72, 541) and incorporated herein by reference, was subcloned into the multiple cloning site of the pVL1393 baculovirus vector (Invitrogen) downstream of the baculovirus polyhedron promoter by standard techniques known to those skilled in the art. This construct is predicted to encode a non-fused, native vpr protein. Transfection of this plasmid along with linearized AcMNPV genomic DNA (BaculoGold, PharMingen) by standard techniques into SF9 (*Spodoptera frugiptera*) insect cells yielded recombinant baculoviruses containing the vpr gene. Twenty four hours after transfection, virus-containing supernatants from transfected cells were applied to new High Five cells (Trichoplusia ni) whose supernatants and cell fractions were then assayed for vpr protein expression by standard techniques. Vpr protein was detected in the supernatants and in the cell fractions of infected cells by ELISA within 12 hours of infection and not in the supernatants or cell fractions of cells infected with baculovirus, prepared identically to the vpr recombinants but lacking a vpr gene. Peak vpr levels in the supernatant were detected at 24 hours post-infection. The reasons for the preferential export of vpr into the baculovirus supernatants is not known. However, export of recombinant proteins is not unusual for this expression system.

Example 29

Partial Purification of vpr Protein

Vpr-containing supernatants were applied to an anti-vpr-peptide affinity column, constructed by standard methods.

Partial purification and concentration was achieved by triethanolamine (pH 11.5) elution followed by DEAE sepharose chromatography by techniques known to those skilled in the art. This material displayed both the monomeric and putative homodimeric forms of vpr with roughly ten times more monomer than dimer observed. The material was used to immunize a rabbit 3 times at 6–8 week intervals, followed by a single immunization with 3 vpr peptides representing amino and carboxyl terminal residues and a central hydrophilic portion of the molecule. The final immunization with vpr peptides served to increase the specific anti-vpr titer of the serum. The resulting serum bound native viral and recombinant baculovirus vpr proteins in Western blot and ELISA and specifically recognized the 3 vpr peptides in ELISA. Optimum dilution of serum for ELISA was 1:10,000. No cross-reactivity with other components of the baculovirus supernatant or to any other proteins was observed by Western blot or ELISA. An affinity column was prepared using this serum and vpr supernatants were applied. The protein eluting from this column displayed three major bands on silver stained or coomassie stained SDS-PAGE gels, representing the monomer and dimer forms of vpr, plus a 50 kDa band which probably represents the lactalbumin present in the cell growth medium nonspecifically bound to the column.

Example 30

Biological Activity of Baculovirus vpr

Recombinant vpr protein can be tested for biological activity in tissue culture. Vpr and control supernatants were dialyzed against PBS and applied to TE671 rhabdomyosarcoma cells. TE671 cells differentiate and cease to proliferate when transfected with the vpr gene or infected with HIV (Gras-Masse et al., supra; Levy et al., supra). Surprisingly, TE671 cells exposed continuously to 20% vpr supernatant ceased proliferation after approximately 3 days and after 7–9 days underwent morphological differentiation similar to that observed following transfection with the HIV-1 vpr gene, including great enlargement, the presence of long processes similar to myotubes, multinucleation and cessation of proliferation. Exposure to greater than 20% supernatant proved to be rapidly fatal to the cells. Incubation of TE671 cells with equal concentrations of control supernatants failed to induce any of these changes. Cells exposed to vpr for 3 days were examined for the presence of adult muscle myosin, a differentiation marker for these cells (Aguanno et al., *Cancer Res*., 1990, 50, 3377). Greater than 90% of cells stained positive using an anti-myosin antibody, demonstrating that the differentiation was along the pathway to which to these cells are committed and is identical to that induced by expression of vpr from within.

Example 31

Melanoma cells were transfected with a nucleic acid molecules that comprised a nucleotide sequence that encoded vpr. In test experiments, transfected cells were selected and implanted into mice. As a control, untransfected melanoma cells were introduced into other mice.

The mice with implanted transfected melanoma cells displayed a vast reduction in the number of tumors developing from the injected cells as compared to the number of tumors developing in control mice. The results from these experiments clearly demonstrated that while vpr did not complete eliminate the tumorigenicity of the melanoma cells, the presence of the vpr gene in the melanoma cells significantly and substantially reduced the tumorigenicity of the cells.

Example 32

Three peptides were synthesized by routine methods. Each peptide is an immunogenic fragment of vpr protein. The first, SEQ ID NO:8, is residues 9–20. The second, SEQ ID NO:9, is residues 41–55. The third, SEQ ID NO:10, is residues 81–96.

Each peptide has been confirmed to be immunogenic in rabbits and mice. The antibodies produced cross-react to vpr.

Pharmaceutical compositions are produced which comprise SEQ ID NO:8, SEQ ID NO:9 and/or SEQ ID NO:10 and a pharmaceutically acceptable carrier or diluent. Administration of such pharmaceutical compositions in an individual suffering from HIV infection results in a immunogenic response that produces antibodies which cross react with vpr. The antibodies thus produced bind to and inactivate vpr present as a result of the HIV infection.

TABLE 1

HIV-1 Constructs Used in Example 1

| Construct | Vector or Derivation | vpr | Differentiation | p24 Production | Characteristics |
|---|---|---|---|---|---|
| pNLpuro | HIV1 pNL43 | + | +++ | +++ | env deletion mutant |
| vpr | pBABE-puro | + | +++ | N/A | |
| vif | pBABE-puro | − | − | N/A | |
| vpu | PBABE-puro | − | − | N/A | |
| nef | pBABE-puro | − | − | N/A | |
| tat | pCV-1 | − | − | N/A | |
| env-rev | pcDNA1/neo | − | − | N/A | env$^{\pm}$, syncytia: ++ |
| pNLpuroΔvpr | pNL43 | − | −/+[a] | +++ | env, deletion mutant |
| pNL43 | pNL43 | + | NT | +++ | env$^{\pm}$, syncytia in TE671Ψ: ++ |
| pNLΔvpr | pNL43 | − | NT | +++ | env$^{\pm}$, syncytia in TE671Ψ: ++ | p24 release into the culture medium was measured 48 hr following transfection, as described in Experimental Procedures.
[a]Transient increase in size in some cells, with reversion of phenotype observed after approximately 6 days, and differentiation in a small subset (5%–10%)
NT, not tested; N/A, not applicable.

What is claimed is:

1. Isolated human immunodeficiency virus Vpr protein produced in eukaryotic cells.

2. A method of identifying whether or not an individual has been infected with human immunodeficiency virus comprising the steps of:
   a) contacting a test sample from said individual with isolated human immunodeficiency virus Vpr protein produced in eukaryotic cells, and
   b) detecting the presence of anti-Vpr antibodies bound to said Vpr, wherein the presence of anti-Vpr antibodies indicates that said individual has been infected with human immunodeficiency virus and the absence of said anti-Vpr antibodies indicates that said individual has not been infected with human immunodeficiency virus.

3. A kit for identifying whether or not an individual has been infected with human immunodeficiency virus comprising
   a) a first container comprising isolated human immunodeficiency virus Vpr protein produced in eukaryotic cells, and
   b) a second container which contains antibodies which specifically bind to Vpr protein produced in eukaryotic cells.

4. The isolated protein of claim 1 wherein said protein is immobilized to a solid phase support.

5. The isolated protein of claim 4, wherein said solid phase support is selected from the group consisting of: nitrocellulose paper, glass, polystyrene, polypropylene, polyethylene, dextran, nylon, amylase, natural and modified cellulose, polyacrylamide, agarose, and magnetite.

6. The isolated protein of claim 4, wherein said solid phase support is nitrocellulose paper or polystyrene.

7. The method of claim 2 wherein said test sample is selected from the group consisting of: blood, cerebral spinal fluid, amniotic fluid, lymph, semen or vaginal fluid.

8. The method of claim 2 wherein said test sample is blood.

9. The method of claim 2 wherein said Vpr protein is immobilized to a solid phase support.

10. The method of claim 9 wherein said solid phase support is selected from the group consisting of: nitrocellulose paper, glass, polystyrene, polypropylene, polyethylene, dextran, nylon, amylases, natural and modified cellulose, polyacrylamide, agarose, and magnetite.

11. The method of claim 9 wherein said solid phase support is nitrocellulose paper or polystyrene.

12. The method of claim 2 comprising the steps of:
   a) contacting said test sample with Vpr protein that is immobilized to a solid phase support, and
   b) the presence of anti-Vpr antibodies bound to said Vpr is detected by
      i) adding anti-human antibody antibodies to said test sample and Vpr protein that is immobilized to a solid phase support; and
      ii) detecting said anti-human antibody antibodies bound to anti-Vpr antibodies that are bound to Vpr protein that is immobilized said solid phase support.

13. The method of claim 12 wherein said anti-human antibodies are labelled.

14. The method of claim 2 further comprising the step of performing a positive control assay, said positive control assay comprising the steps of:
   a) contacting a positive control sample with Vpr protein produced in eukaryotic cells, wherein said positive control sample comprises positive control antibodies which are antibodies that bind to Vpr produced in eukaryotic cells; and
   b) detecting the presence of said positive control antibodies bound to said Vpr produced in eukaryotic cells.

15. The method of claim 2 comprising the steps of:
   a) contacting said test sample with Vpr protein that is immobilized to a solid phase support, and
   b) detecting the presence of anti-Vpr antibodies bound to said Vpr by:
      i) washing said solid phase support;
      ii) adding to said test sample and Vpr protein that is immobilized to said solid phase support, labelled antibodies that bind to human antibody Fc region;
      iii) washing said solid phase support;
      iv) detecting said anti-human antibodies bound to said solid phase support.

16. The method of claim 15 wherein said anti-human antibodies are horse radish peroxidase labelled goat anti-human antibodies.

17. The kit of claim 3 wherein said Vpr protein is immobilized to a solid phase support.

18. The kit of claim 17 wherein said solid phase support is selected from the group consisting of: nitrocellulose paper, glass, polystyrene, polypropylene, polyethylene, dextran, nylon, amylases, natural and modified cellulose, polyacrylamide, agarose, and magnetite.

19. The kit of claim 17 wherein said solid phase support is nitrocellulose paper or polystyrene.

20. The kit of claim 3 further comprising a positive control which contains antibodies which specifically bind Vpr produced in eukaryotic cells.

21. An in vitro method of identifying individuals who have been exposed to the human immunodeficiency virus comprising the following steps:
   (i) preparing a test sample from said individual;
   (ii) admixing the test sample of step (i) with isolated eukaryotically expressed human immunodeficiency virus Vpr;
   (iii) detecting the presence of anti-Vpr antibodies bound to said Vpr;
wherein the presence of said anti-Vpr antibodies indicates that said individual has been exposed to the human immunodeficiency virus.

22. The method of claim 21 wherein said test sample is selected from the group consisting of: blood, cerebral spinal fluid, amniotic fluid, lymph, semen or vaginal fluid.

23. The method of claim 21 wherein said test sample is blood.

24. The method of claim 21 wherein said Vpr protein is immobilized to a solid phase support.

25. The method of claim 24 wherein said solid phase support is selected from the group consisting of: nitrocellulose paper, glass, polystyrene, polypropylene, polyethylene, dextran, nylon, amylases, natural and modified cellulose, polyacrylamide, agarose, and magnetite.

26. The method of claim 24 wherein said solid phase support is nitrocellulose paper or polystyrene.

27. An in vitro method of identifying individuals who have been exposed to the human immunodeficiency virus comprising the following steps:
(i) preparing a test sample from said individual;
(ii) admixing the test sample of step (i) with isolated eukaryotically expressed human immunodeficiency virus Vpr immobilized to a solid phase support;
(iii) allowing antibodies, if present in the test sample, to bind to and form an immune complex with said immobilized Vpr;
(iv) detecting the presence of anti-Vpr antibodies bound to said Vpr by admixing a labeled anti-human secondary antibody with the immune complexes of step (iii); wherein the presence of said anti-Vpr antibodies indicates that said individual has been exposed to the human immunodeficiency virus.

28. The method of claim 27 wherein said anti-human secondary antibody is a goat anti-human antibody labeled with horseradish peroxidase.

29. A diagnostic kit for identifying individuals who have been exposed to the human immunodeficiency virus comprising the following components:
(i) a container comprising isolated eukaryotically expressed human immunodeficiency virus Vpr
(ii) a container comprising a labeled anti-human secondary antibody;
(iii) a container comprising Vpr-specific antibodies;
(iv) a container comprising antibodies that do not bind to Vpr; and,
(v) a container comprising detection reagents.

30. The kit of claim 29 wherein said Vpr is immobilized to a solid-phase support.

31. The kit of claim 30 wherein said solid phase support is selected from the group consisting of: nitrocellulose paper, glass, polystyrene, polypropylene, polyethylene, dextran, nylon, amylases, natural and modified cellulose, polyacrylamide, agarose, and magnetite.

32. The kit of claim 30 wherein said solid phase support is nitrocellulose paper or polystyrene.

* * * * *

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
       (A) LENGTH: 28 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:1:

ggcggctcga ggatccgccg ccaccatg                                              28

(2) INFORMATION FOR SEQ ID NO:2:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:2:

ggggcttgtt ccatggtggc                                                       20

(2) INFORMATION FOR SEQ ID NO:3:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:3:

ccgcggatcc taggatctac tggc                                                  24

(2) INFORMATION FOR SEQ ID NO:4:

(i) SEQUENCE CHARACTERISTICS:
       (A) LENGTH:  21 amino acids
       (B) TYPE: amino acid
       (D) TOPOLOGY: linear (ii) MOLECULE TYPE: peptide (xi) SEQUENCE DESCRIPTION: SEQ ID NO:4:

Cys Glu Gln Ala Pro Glu Asp Gln Gly Pro Gln Arg Glu Pro His Asn
  1               5                  10                  15

Glu Trp Thr Leu Glu
            20

(2) INFORMATION FOR SEQ ID NO:5:

(i) SEQUENCE CHARACTERISTICS:
       (A) LENGTH: 12 amino acids
       (B) TYPE: amino acid
       (D) TOPOLOGY: linear (ii) MOLECULE TYPE: peptide

```
        (xi) SEQUENCE DESCRIPTION: SEQ ID NO:5:

Gly Pro Gln Arg Glu Pro His Asn Glu Trp Thr Leu
1               5                   10

(2) INFORMATION FOR SEQ ID NO:6:

(i) SEQUENCE CHARACTERISTICS:
            (A) LENGTH: 14 amino acids
            (B) TYPE: amino acid
            (D) TOPOLOGY: linear (ii) MOLECULE TYPE: peptide (xi) SEQUENCE DESCRIPTION: SEQ ID NO:6:

Gly Leu Gly Gln His Ile Tyr Glu Thr Gly Asp Thr Trp Ala
1               5                   10

(2) INFORMATION FOR SEQ ID NO:7:

(i) SEQUENCE CHARACTERISTICS:
            (A) LENGTH: 16 amino acids
            (B) TYPE: amino acid
            (D) TOPOLOGY: linear (ii) MOLECULE TYPE: peptide (xi) SEQUENCE DESCRIPTION: SEQ ID NO:7:

Ile Gly Val Thr Gln Gln Arg Arg Gln Arg Asp Gly Ala Ser Arg Ser
1               5                   10                  15

(2) INFORMATION FOR SEQ ID NO:8:

(i) SEQUENCE CHARACTERISTICS:
            (A) LENGTH:  12 amino acids
            (B) TYPE: amino acid
            (D) TOPOLOGY: linear (ii) MOLECULE TYPE: peptide (xi) SEQUENCE DESCRIPTION: SEQ ID NO:8:

Gly Pro Gln Arg Glu Pro His Asn Glu Trp Thr Leu
1               5                   10

(2) INFORMATION FOR SEQ ID NO:9:

(i) SEQUENCE CHARACTERISTICS:
            (A) LENGTH: 15 amino acids
            (B) TYPE: amino acid
            (D) TOPOLOGY: linear (ii) MOLECULE TYPE: peptide (xi) SEQUENCE DESCRIPTION: SEQ ID NO:9:

Gly Leu Gly Gln His Ile Tyr Glu Thr Tyr Gly Asp Thr Trp Ala
1               5                   10                  15

(2) INFORMATION FOR SEQ ID NO:10:

(i) SEQUENCE CHARACTERISTICS:
            (A) LENGTH: 16 amino acids
            (B) TYPE: amino acid
            (D) TOPOLOGY: linear
```

```
    (ii) MOLECULE TYPE: peptide (xi) SEQUENCE DESCRIPTION: SEQ ID NO:10:

Ile Gly Val Thr Gln Gln Arg Arg Ala Arg Asn Gly Ala Ser Arg Ser
1               5                   10                  15
```